United States Patent
DeYoung

(10) Patent No.: US 11,439,360 B2
(45) Date of Patent: Sep. 13, 2022

(54) MEDICAL PROCEDURE DRAPING SYSTEM

(71) Applicant: Hologic, Inc., Marlborough, MA (US)

(72) Inventor: Thomas W. DeYoung, Hopewell Junction, NY (US)

(73) Assignee: Hologic, Inc., Marlborough, MA (US)

( * ) Notice: Subject to any disclaimer, the term of this patent is extended or adjusted under 35 U.S.C. 154(b) by 602 days.

(21) Appl. No.: 16/103,989

(22) Filed: Aug. 16, 2018

(65) Prior Publication Data

US 2019/0167220 A1 Jun. 6, 2019

Related U.S. Application Data

(60) Provisional application No. 62/546,449, filed on Aug. 16, 2017.

(51) Int. Cl.
| | |
|---|---|
| *A61B 6/00* | (2006.01) |
| *A61B 6/04* | (2006.01) |
| *A61B 10/02* | (2006.01) |
| *A61B 46/20* | (2016.01) |
| *A61B 46/10* | (2016.01) |
| *A61B 5/053* | (2021.01) |

(52) U.S. Cl.
CPC .............. *A61B 6/502* (2013.01); *A61B 6/04* (2013.01); *A61B 10/0233* (2013.01); *A61B 46/10* (2016.02); *A61B 46/20* (2016.02); *A61B 5/053* (2013.01); *A61B 2046/205* (2016.02)

(58) Field of Classification Search
CPC .......... A61B 6/502; A61B 46/10; A61B 46/20; A61B 46/00
See application file for complete search history.

(56) References Cited

U.S. PATENT DOCUMENTS

| | | | | | |
|---|---|---|---|---|---|
| 3,669,106 | A | * | 6/1972 | Schrading | A61B 46/00 128/853 |
| 4,024,862 | A | * | 5/1977 | Collins | A61B 46/00 128/854 |
| 4,040,418 | A | * | 8/1977 | Collins | A61B 46/23 128/852 |

(Continued)

OTHER PUBLICATIONS

User Instructions for the MultiCare Drape System, Hologic, Inc., Bedford, MA (2006).

(Continued)

*Primary Examiner* — David P Porta
*Assistant Examiner* — Djura Malevic
(74) *Attorney, Agent, or Firm* — Merchant & Gould P.C.

(57) ABSTRACT

A draping system for use with a medical apparatus, such as a prone breast biopsy system. The draping system may be in the form of a kit ready to be installed on the medical apparatus and may include one or more of a first drape, a second drape, and a third drape. The first drape may include a mat and a protuberance, the mat and the protuberance being coupled together. The protuberance may be configured to receive a paddle mount of the medical apparatus. The mat may have a distal end configured to be secured to a breast support platform of the medical apparatus just below an image receptor. The second drape may include a mat having a distal end configured to be mounted on a compression paddle of the medical apparatus. The third drape may be configured to be inserted over the control panel of the medical apparatus.

20 Claims, 17 Drawing Sheets

(56) References Cited

U.S. PATENT DOCUMENTS

| | | | | |
|---|---|---|---|---|
| 4,089,331 | A * | 5/1978 | Hartigan | A61B 46/00 128/850 |
| 4,134,398 | A * | 1/1979 | Scrivens | A61B 46/23 128/852 |
| 4,275,720 | A * | 6/1981 | Wichman | A61B 46/00 128/853 |
| 4,323,062 | A * | 4/1982 | Canty | A61M 25/02 128/852 |
| 4,476,860 | A * | 10/1984 | Collins | A61B 46/23 128/852 |
| 4,905,710 | A * | 3/1990 | Jones | A61B 46/00 128/849 |
| 4,956,966 | A * | 9/1990 | Patterson | A01D 41/14 56/181 |
| 4,981,142 | A * | 1/1991 | Dachman | A61B 6/0414 128/897 |
| 5,222,507 | A * | 6/1993 | Taylor | A61B 46/00 128/849 |
| 5,345,946 | A * | 9/1994 | Butterworth | A61B 46/00 128/853 |
| 5,409,018 | A * | 4/1995 | Mills | A61B 46/00 128/849 |
| 5,464,024 | A * | 11/1995 | Mills | A61B 46/00 128/849 |
| 5,490,524 | A * | 2/1996 | Williams | A61B 46/10 128/849 |
| 5,522,403 | A * | 6/1996 | Bark | A61B 46/00 128/849 |
| 5,540,979 | A * | 7/1996 | Yahiaoui | D04H 1/559 428/212 |
| 5,635,134 | A * | 6/1997 | Bourne | A61L 2/07 422/26 |
| 5,640,975 | A * | 6/1997 | Diao | A61B 46/00 128/849 |
| 5,704,370 | A * | 1/1998 | Gawarecki | A61G 13/10 128/849 |
| 5,778,889 | A * | 7/1998 | Jascomb | A61B 46/00 128/849 |
| 5,845,641 | A * | 12/1998 | Pinney | A61B 46/00 128/849 |
| 5,901,706 | A * | 5/1999 | Griesbach | B32B 5/022 128/849 |
| 5,947,122 | A * | 9/1999 | McDonald | A61B 46/00 128/849 |
| 5,960,794 | A * | 10/1999 | Shaw | A61B 46/30 128/849 |
| 5,991,666 | A * | 11/1999 | Vought | A61F 7/00 128/849 |
| 6,032,670 | A * | 3/2000 | Miller | A61B 46/00 128/849 |
| 6,199,553 | B1 * | 3/2001 | Hafer | A61B 46/00 128/849 |
| 6,279,578 | B1 * | 8/2001 | Hinley, Jr. | A61B 46/40 128/849 |
| 6,282,264 | B1 * | 8/2001 | Smith | A61B 6/4233 378/189 |
| 6,283,125 | B1 * | 9/2001 | McNeirney | A61B 46/10 128/853 |
| 6,298,855 | B1 * | 10/2001 | Baird | A61B 46/00 128/849 |
| 6,314,958 | B1 * | 11/2001 | Harroll | A61B 46/20 128/849 |
| 6,406,674 | B1 * | 6/2002 | Bourne | A61L 2/26 206/439 |
| 6,440,063 | B1 * | 8/2002 | Beane | A61B 42/10 600/207 |
| 6,497,233 | B1 * | 12/2002 | DeAngelis | A61B 50/13 128/849 |
| 6,612,310 | B2 * | 9/2003 | Sklar | A61B 46/10 128/849 |
| 6,615,836 | B1 * | 9/2003 | Griesbach | A61B 46/23 128/849 |
| 6,851,851 | B2 * | 2/2005 | Smith | A61B 6/06 378/189 |
| 6,874,505 | B1 * | 4/2005 | Fenwick | A61B 46/23 128/849 |
| 7,044,132 | B2 * | 5/2006 | Masini | A61B 46/00 128/849 |
| 7,096,870 | B2 * | 8/2006 | Lamprich | A61B 46/23 128/849 |
| 7,305,991 | B2 * | 12/2007 | Santilli | A61B 50/30 128/849 |
| 7,343,919 | B2 * | 3/2008 | Czajka | A61B 46/20 128/849 |
| 7,654,266 | B2 * | 2/2010 | Corbitt, Jr. | A61B 46/30 128/849 |
| 7,727,244 | B2 * | 6/2010 | Orban, III | A61B 46/10 606/130 |
| 7,775,213 | B2 * | 8/2010 | Henke-Sarmento | A61B 46/10 128/852 |
| 7,922,983 | B2 * | 4/2011 | Prokash | A61L 2/26 422/294 |
| 8,011,371 | B2 * | 9/2011 | Rotolo | A61B 46/00 128/854 |
| 8,079,365 | B2 * | 12/2011 | Block | A61B 46/00 128/853 |
| 8,196,586 | B2 * | 6/2012 | Henke-Sarmento | A61B 46/10 128/852 |
| 8,281,790 | B2 * | 10/2012 | Gustafsson | A61B 46/00 128/849 |
| 8,813,755 | B2 * | 8/2014 | Hoffmann | A61B 46/00 128/849 |
| D745,684 | S * | 12/2015 | Henke-Sarmento | D24/184 |
| 9,393,075 | B2 * | 7/2016 | Ghosh | A61B 46/10 |
| 9,820,751 | B2 * | 11/2017 | Haines | A61B 17/1322 |
| 9,937,015 | B2 * | 4/2018 | Haines | A61B 46/00 |
| 10,039,610 | B2 * | 8/2018 | Allen | A61B 46/00 |
| 10,092,358 | B2 * | 10/2018 | Defreitas | A61B 6/0435 |
| 10,123,838 | B2 * | 11/2018 | Berdia | A61B 46/00 |
| 10,265,133 | B1 * | 4/2019 | McClellan | A61B 46/40 |
| 10,271,916 | B2 * | 4/2019 | Allen | A61B 46/00 |
| D851,772 | S * | 6/2019 | Haines | D24/184 |
| 10,455,872 | B2 * | 10/2019 | Pasko | A41D 13/129 |
| 10,456,213 | B2 * | 10/2019 | Defreitas | A61B 6/025 |
| 10,729,507 | B2 * | 8/2020 | Beale | A61B 46/40 |
| 2006/0150987 | A1 * | 7/2006 | Dillon | A61B 46/00 128/849 |
| 2007/0079834 | A1 * | 4/2007 | Reyes | A61B 46/20 128/853 |
| 2007/0102005 | A1 * | 5/2007 | Bonutti | A61B 17/1703 128/849 |
| 2007/0135784 | A1 * | 6/2007 | Tankersley | A61B 46/00 604/357 |
| 2008/0006278 | A1 * | 1/2008 | Henke-Sarmento | A61B 46/10 128/849 |
| 2008/0045833 | A1 * | 2/2008 | Defreitas | A61B 10/0275 600/429 |
| 2009/0255541 | A1 * | 10/2009 | Kaska | A61B 46/10 128/853 |
| 2010/0031966 | A1 * | 2/2010 | Allen | A61B 46/00 128/851 |
| 2010/0326449 | A1 * | 12/2010 | Henke-Sarmento | A61B 46/10 128/852 |
| 2016/0022364 | A1 * | 1/2016 | Defreitas | A61B 90/11 600/429 |

OTHER PUBLICATIONS

Promotional literature for the Hologic Affirm Prone Biopsy System, Hologic, Inc., Marlborough, MA (2016).

Spec sheet for Beautiful LF 20089 nonwoven laminate, Beautiful Nonwoven Co. Ltd., Nanhai Foshan City, China (2016).

Printout of YouTube webpage for instructional video on how to install the QSUM FT301 table draping and FA201A autoguide draping, https://www.youtube.com/watch?v=w0_Cwl3-9Xc (2017).

* cited by examiner

MEDICAL PROCEDURE DRAPING SYSTEM

CROSS-REFERENCE TO RELATED APPLICATIONS

The present application claims the benefit under 35 U.S.C. 119(e) of U.S. Provisional Patent Application No. 62/546,449, inventor Thomas W. DeYoung, filed Aug. 16, 2017, the disclosure of which is incorporated herein by reference.

BACKGROUND

The present invention relates generally to medical apparatuses designed for use in examination, surgery and/or other medical procedures and relates more particularly to draping systems for use with such apparatuses.

Medical imaging technologies, such as stereotactic x-ray, fluoroscopy, computed tomography, ultrasound, nuclear medicine, and magnetic resonance imaging, are often useful in the detection of small abnormalities in the body of a patient. The discovery of certain abnormalities using such imaging techniques may prompt the performance of a biopsy procedure. Such a procedure typically involves obtaining a tissue sample for subsequent lab analysis and may be useful in diagnosing and/or treating patients suspected of having cancerous tumors, pre-malignant conditions or other diseases or disorders. The biopsy may be either an open surgical procedure or a percutaneous procedure. Percutaneous biopsy is often preferable to an open surgical biopsy for small abnormalities located deep within the body because a percutaneous biopsy typically removes a smaller amount of tissue. For example, a biopsy needle can be used to remove individual cells or clusters of cells, in the case of fine needle aspiration (FNA), or a core or fragment of tissue, in the case of a core biopsy.

A breast biopsy apparatus having a table where a patient is laying down is used for performing a breast biopsy for a patient in a prone position. In U.S. Patent Application Publication No. US 2016/0022364 A1, inventors DeFreitas et al., published Jan. 28, 2016, which is incorporated herein by reference, there is disclosed a particular apparatus for performing tomotactic guided breast biopsy for a patient in a prone position. Using such a system, a patient lays down in the prone position with the patient's breast extending through an aperture where it can be accessed for imaging and tissue excision. Because the patient is laying in prone, due to gravity, a blood vein coming in contact with the needle, or for other reasons, there may be significant amount of blood traveling from the patient's breast to the biopsy apparatus. Such flow of blood may disturb the patient and contaminate the equipment, making it difficult to clean. Additionally, the blood could corrode the sensitive imaging equipment.

Specific parts of the biopsy apparatus will now be described in more detail. As seen, for example, in FIGS. 1 through 7 of the aforementioned publication (which publication is hereinafter referred to as "the '364 publication"), the apparatus of the '364 publication includes a biopsy table, a tomosynthesis imaging system, a breast support assembly, and a stage arm assembly. The biopsy table includes a rigid platform and a footed base, the footed base supporting the rigid platform. The footed base is offset to one side of the platform such that an area beneath the platform is available for positioning both a breast of the patient on which the biopsy is to be performed and equipment for performing the biopsy. In particular, the platform includes an aperture that is positioned and configured to enable a breast of the patient to extend below the platform when the patient is situated on the platform in a prone position. An equipment support is cantilevered from the footed base beneath the rigid platform and may be statically or repositionably connected to the footed base. The tomosynthesis imaging system, which is positioned below the rigid platform and is pivotally mounted on the equipment support, includes an x-ray energy source and an x-ray energy receptor. The source and the receptor are aligned such that the receptor detects energy emitted by the source. The breast support assembly, which is positioned below the rigid platform and is pivotally mounted on the equipment support independently of the tomosynthesis imaging system, is used to place a breast in compression and includes a breast support platform (behind which the x-ray energy receptor is positioned) and a compression paddle. The compression paddle is linearly movable relative to the breast support platform in order to compress a breast therebetween. The stage arm assembly, which is positioned below the rigid platform of the table and is pivotally mounted on the equipment support independently of the tomosynthesis imaging system and the breast support assembly, includes a gun mount and a biopsy gun. The gun mount is coupled to a carriage slide assembly, which may be selectively moved towards or away from a compressed breast. The biopsy gun is removably mounted on the gun mount.

The apparatus of the '364 publication is configured so that a biopsy may be performed in either of two alternative modes: an anterior-approach mode and a lateral-approach mode. In the anterior-approach mode, the stage arm assembly is positioned relative to the breast support assembly so that the biopsy gun is movable along an axis towards and away from the breast-engaging surface of the compression paddle. A transverse opening is provided in the compression paddle, and the needle of the biopsy gun is aligned with this opening; consequently, movement of the biopsy gun in the anterior-approach mode causes the needle of the biopsy gun to pass through the transverse opening in the compression paddle and then to enter the breast anteriorly. In the lateral-approach mode, the stage arm assembly is positioned relative to the breast support assembly so that the biopsy gun is movable along an axis towards and away from the side of the breast. Consequently, movement of the biopsy gun in the lateral-approach mode causes the needle to enter the breast laterally without passing through the compression paddle. Selection of the anterior-approach mode or the lateral-approach mode may depend on one or more factors, such as the location of the cells or tissue to be biopsied and the size or thickness of the breast to be biopsied. For example, where the breast to be biopsied is thin, the lateral-approach mode may be preferred in order to avoid the possibility that the biopsy needle may pass entirely through the breast and damage the breast support platform (or the x-ray receptor positioned therebehind).

A commercial embodiment of the above-described apparatus is available from the present applicant, Hologic, Inc. (Marlborough, Mass.), as AFFIRM® prone biopsy system. The aforementioned system comprises a plurality of different compression paddles, both to accommodate breasts of different sizes and to accommodate operation of the apparatus in either the anterior-approach mode or the lateral-approach mode. In use, a desired compression paddle is selected from the plurality of different compression paddles and is mounted on a paddle mount. (The paddle mount, in turn, is slidably mounted on a platform.) In order that the apparatus may identify which type of compression paddle, from among the various different compression paddles, is mounted on the paddle mount, each type of compression paddle is equipped with a distinctive number of magnets, and the paddle mount is equipped with a sensing mechanism, which includes Hall-effect sensors, for detecting the number of magnets on a compression paddle that is mounted on the paddle mount.

As described above, where the above-described apparatus is used to perform a biopsy, such fluids can flow from the needle insertion site to various locations within the apparatus. This may be undesirable as such fluids not only may biologically contaminate one or more components of the apparatus but also may compromise the performance of one or more components of the apparatus.

SUMMARY

It is an object of the present invention to provide a novel draping system that is suitable for use with a medical apparatus, in particular, a prone biopsy system.

Therefore, according to one embodiment, there is provided a draping system suitable for use with a prone biopsy system, the prone biopsy system comprising a paddle mount, the draping system comprising a first drape, the first drape comprising a first mat and a protuberance, the protuberance extending upwardly from the first mat and being configured to be inserted over the paddle mount, wherein the first mat and the protuberance comprise different materials.

According to a further embodiment, the protuberance may be optically transparent or translucent.

According to a further embodiment, the protuberance may be constructed so as not to impede the mounting of a compression paddle to the paddle mount after the paddle mount has been covered by the protuberance.

According to a further embodiment, the paddle mount may comprise a sensing mechanism including Hall-effect sensors for detecting the type of compression paddle mounted thereon, and the protuberance may be constructed so as not to impede operation of the sensing mechanism.

According to a further embodiment, the protuberance may be made of a clear polymer film.

According to a further embodiment, the first mat may comprise a length, the protuberance may comprise a length, a width, and a perimeter, the length of the protuberance may be perpendicular to the length of the first mat, the protuberance may be positioned off-center relative to the length of the first mat so as to be disposed closer to a first end of the first mat than to a second end of the first mat, the width of the protuberance may be substantially less than the length of the first mat, and the perimeter of the protuberance may be completely surrounded by and sealed to the first mat.

According to a further embodiment, the first mat may comprise an absorbent material. Applicants have discovered that having a drape comprising two different materials to cover different portions of the breast biopsy apparatus could be advantageous. For example, having a protuberance that comprises a clear polymer film could minimize the interference with the operation of the imaging and sensing mechanism while having a first mat that comprises an absorbent material could allow for the absorption of blood from the patient and minimize damage to the sensitive components of the apparatus. In addition, the draping system is preferably disposable which allows for fast, and highly sanitary clean up between biopsies. This may reduce the risk of infection of the patient, provide cleanup advantages for the medical facility, and decrease the time between procedures. Where the first mat and the protuberance are coupled together, there may be minimal potential for blood to leak between the parts. In addition, because the absorbent material of the first mat may completely surround the clear material of the protuberance, more of the blood, even the blood traveling down the protuberance, may be absorbed by the first mat.

According to a further embodiment, the first drape may further comprise a first skirt, and the first skirt may extend upwardly from the first mat around at least a portion of the periphery of the first mat.

According to a further embodiment, the first mat and the first skirt may be integrally formed. The skirt may provide further advantages, including minimizing any further leakage from the first mat. In most cases the absorbent material of the first mat may be sufficient to absorb the blood from the patient. However, in some cases, there may still be blood that continues to travel down the first mat. The skirt may further limit any blood from escaping the drape system. Instead, the skirt may allow the blood to pool, so that it can be absorbed by the absorbable material of the drape.

According to a further embodiment, the prone biopsy system may further comprise a breast support platform behind which an image receptor is positioned, and the first mat may be configured to be secured at an end thereof to the breast support platform just below the image receptor. The first mat is preferably secured to the support platform such that movement of the secured end of the first mat relative to the support platform may be prevented during the procedure and while the biopsy apparatus is moving through the compression motion. It is preferably secured in a way that may allow it to be easily removed from the prone biopsy system with minimal effort from the medical personnel so that the first drape can be disposed. For example, the first mat may be secured to the support platform with a strip of double-sided adhesive tape disposed on the bottom of the first mat at an end thereof.

According to a further embodiment, the first mat may be configured to form at least one fold when the paddle mount is moved to a breast compressing position. The at least one fold may allow for the first drape to remain in place while the compression paddle moves into place. The first drape is designed so that it preferably remains attached to the prone biopsy system while in both compressed and uncompressed states and while the paddle mount is moving. In addition, the at least one fold may serve to further prevent travel of blood and increase absorption. The first drape is designed such that the at least one fold is preferably formed right below the breast.

According to a further embodiment, the first drape may further comprise a strip of absorbent material, the strip of absorbent material may be secured to the first mat, and the strip of absorbent material may comprise a higher absorbing material than the material of the first mat.

According to a further embodiment, the strip of absorbent material may comprise a superabsorbent polymer.

According to a further embodiment, the strip of absorbent material may be disposed along the length of the protuberance and may be positioned at a location intermediate the protuberance and the second end of the first mat so as to be positioned below a breast when the paddle mount is moved to a breast compressing position. The absorbent material may allow for absorption of blood in an area that is likely to receive more blood flow as it is positioned right below the compressed breast and adjacent to the compression paddle.

According to a further embodiment, the prone biopsy system may further comprise a compression paddle, wherein the compression paddle may be mountable on the paddle mount, and the draping system may further comprise a second drape, wherein the second drape may comprise a second mat and wherein the second mat may comprise a distal end configured to be fixedly mounted on the compression paddle when the compression paddle is mounted on the paddle mount. A purpose of the second mat is to absorb blood traveling on the other side of the compression paddle from the excision site and protect from blood traveling down from the stage arm assembly.

According to a further embodiment, the prone biopsy system may further comprise a stage arm assembly, the second mat may be configured to cover at least a portion of the stage arm assembly, and the second mat may be provided with one or more perforations for use in separating the second mat into a plurality of pieces.

According to a further embodiment, the second drape may further comprise a second skirt, and the second skirt may extend upwardly from the second mat around at least a portion of the periphery of the second mat. Similar to above, the second skirt may serve to protect from blood escaping from the second mat and to similarly pool at the edge of the second mat, allowing it to be absorbed into the second mat.

According to a further embodiment, the second mat and the second skirt may be integrally formed.

According to a further embodiment, the second mat may be provided with one or more perforations for use in separating the second mat into a plurality of pieces.

According to a further embodiment, the prone biopsy system may further comprise a control panel, and the draping system may further comprise a third drape, wherein the third drape may be configured to substantially encapsulate the control panel.

According to a further embodiment, the first mat may comprise a laminate of an absorbent nonwoven fabric and a first liquid-impervious material, the protuberance may comprise a second liquid-impervious material, and the first and second liquid-impervious materials may be heat-sealable to one another.

According to another embodiment, there is provided a draping system for use with a prone biopsy system, the draping system comprising a first drape, the first drape being configured to cover at least a first portion of the prone biopsy system, the first drape comprising a first mat and a first skirt, the first skirt extending upwardly from the first mat around at least a portion of the periphery of the first mat.

According to a further embodiment, the first mat may be configured to comprise a first side, a second side, and a first end, the first end may interconnect the first side and the second side, and the first skirt may extend upwardly from at least portions of each of the first side, the second side, and the first end.

According to a further embodiment, the first skirt may extend upwardly from substantially the entirety of each of the first side, the second side, and the first end.

According to a further embodiment, the first mat and the first skirt may be integrally formed.

According to a further embodiment, the first mat and the first skirt may comprise an absorbent material.

According to a further embodiment, the prone biopsy system may comprise a paddle mount, and the first drape may be configured to cover the paddle mount.

According to a further embodiment, the first mat may comprise a transverse opening, the first drape may further comprise a protuberance mounted within the transverse opening, and the protuberance may be configured to receive the paddle mount.

According to a further embodiment, the draping system may further comprise a second drape, the second drape may be configured to cover at least a second portion of the prone biopsy system, the second drape may comprise a second mat and a second skirt, and the second skirt may extend upwardly from the second mat around at least a portion of the periphery of the second mat.

According to a further embodiment, the second mat and the second skirt may be integrally formed.

According to a further embodiment, the second mat and the second skirt may comprise an absorbent material.

According to a further embodiment, the prone biopsy system may comprise a stage arm assembly, and the second drape may be configured to cover at least a portion of the stage arm assembly.

According to a further embodiment, the prone biopsy system may further comprise a compression paddle, and the second mat may comprise a distal end configured to be fixedly mounted on the compression paddle.

According to a further embodiment, the second mat may be provided with one or more perforations for use in separating the second mat into a plurality of pieces.

According to yet another embodiment, there is provided a draping system for use with a prone biopsy system, the prone biopsy system comprising a paddle mount, the draping system comprising a first drape, the first drape comprising a first member and a second member, the first member comprising a first mat having a first transverse opening, the second member comprising a protuberance and a flange, the protuberance extending through the first transverse opening of the first mat and being configured to receive the paddle mount, the flange being used to couple the protuberance to the first mat.

According to a further embodiment, the flange and the first mat may form a liquid-tight seal around the entirety of the protuberance.

According to a further embodiment, the first member may further comprise a first skirt, and the first skirt may extend upwardly from the first mat around at least a portion of the periphery of the first mat.

According to a further embodiment, the first mat and the first skirt may be integrally formed.

According to a further embodiment, the first member may comprise a laminate of an absorbent nonwoven fabric and a first liquid-impervious material, and the second member may comprise a second liquid-impervious material, wherein the first and second liquid-impervious materials may be heat-sealable to one another.

According to a further embodiment, the second member may comprise a clear, flexible polymer film, whereby the mounting of a compression paddle to the paddle mount after the paddle mount has been covered by the protuberance is not impeded and whereby operation of a Hall-effect sensing mechanism disposed within the paddle mount for detecting the compression paddle is not impeded.

According to a further embodiment, the prone biopsy system may further comprise a breast support platform behind which an image receptor is positioned and wherein the first drape may further comprise a strip of adhesive tape for securing a first end of the first mat to the breast support platform just below the image receptor, wherein the first mat may be dimensioned so as to form at least one fold below a compressed breast when the paddle mount is moved to a breast compressing position, and wherein the first drape may further comprise a strip of absorbent material secured to the first mat, the strip of absorbent material being disposed on the first mat so as to be positioned below the compressed breast.

According to a further embodiment, the prone biopsy system may further comprise a compression paddle and a stage arm assembly, wherein the compression paddle may be mountable on the paddle mount, and the draping system may further comprise a second drape, wherein the second drape may comprise a second mat, wherein the second mat may be configured to cover at least a portion of the stage arm assembly, wherein the second mat may comprise a distal end, and wherein the distal end may be configured to be fixedly mounted on the compression paddle when the compression paddle is mounted on the paddle mount. The second mat may further comprise one or more perforations for use in separating the second mat into a plurality of pieces, and the second drape may further comprise a second skirt that may extend upwardly from the second mat around at least a portion of the periphery of the second mat.

For purposes of the present specification and claims, various relational terms like "top," "bottom," "proximal," "distal," "upper," "lower," "front," and "rear" may be used to describe the present invention when said invention is positioned in or viewed from a given orientation. It is to be understood that, by altering the orientation of the invention, certain relational terms may need to be adjusted accordingly.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numerals represent like parts:

FIGS. 4(a) and 4(b) are side and bottom views, respectively, of the third drape shown in

FIG. 1;

DETAILED DESCRIPTION

Figure 1:
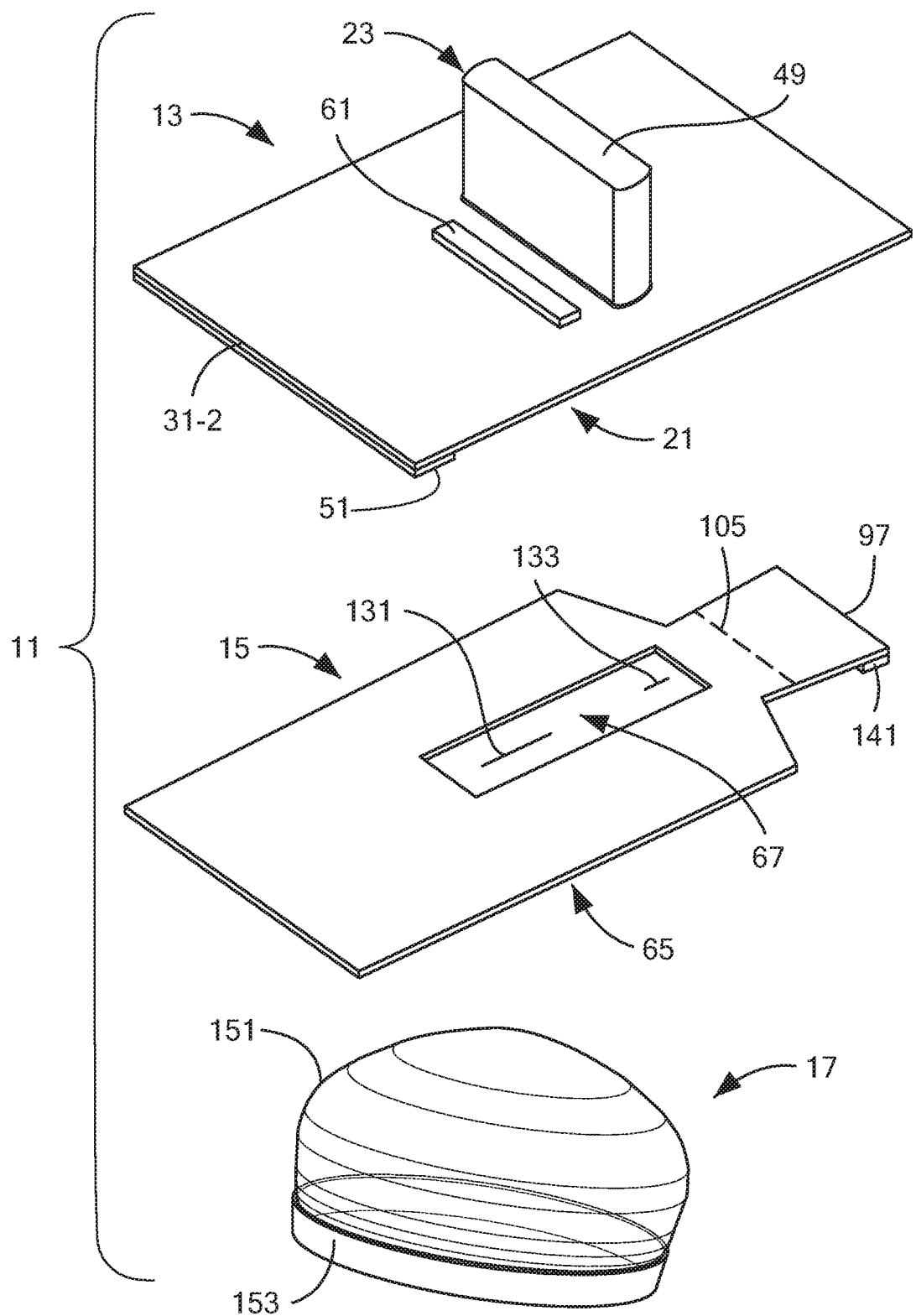
FIG. 1 is a perspective view of a first embodiment of a draping system that is suitable for use with a medical apparatus, in particular, a prone biopsy system, the draping system being constructed according to the present invention.

Referring now to FIG. 1, there is shown a perspective view of a first embodiment of a draping system that is suitable for use with a medical apparatus, in particular, a prone biopsy system, the draping system being constructed according to the present invention and being represented generally by reference numeral 11. For clarity, certain details of draping system 11 that are discussed elsewhere in this application or that are not critical to an understanding of the invention may not be shown in FIG. 1 or may be shown therein in a simplified manner.

Draping system 11, which may be in the form of an assembly or kit ready to be installed on a prone biopsy system, may comprise one or more drapes. More specifically, in the present embodiment, draping system 11 may comprise a first drape 13, a second drape 15, and a third drape 17. A two-part draping system having a first drape and a second drape is advantageous because it allows for better aligning the draping system to the areas that receive the most fluid, while limiting movement of the drape during the procedure, and limiting interference of the draping system with the imaging and sensing functions. In addition, the draping system can be designed for a targeted fit to the geometries of the prone biopsy system. Such precise fitting could allow for quick set up and removal of the drape system before and after the biopsy procedure, saving medical technicians time and allowing them to schedule more procedures on the same biopsy apparatus.

Figure 2A:
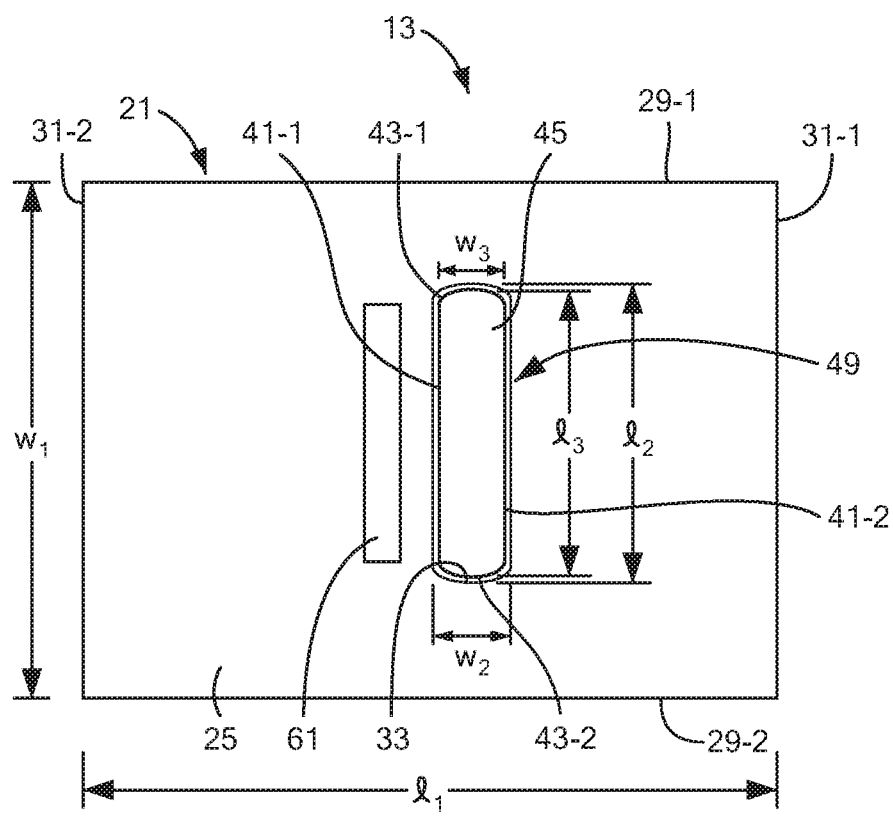
FIGS. 2(a) through 2(c) are top, bottom, and side views, respectively, of the first drape shown in FIG. 1.
Figure 2B:
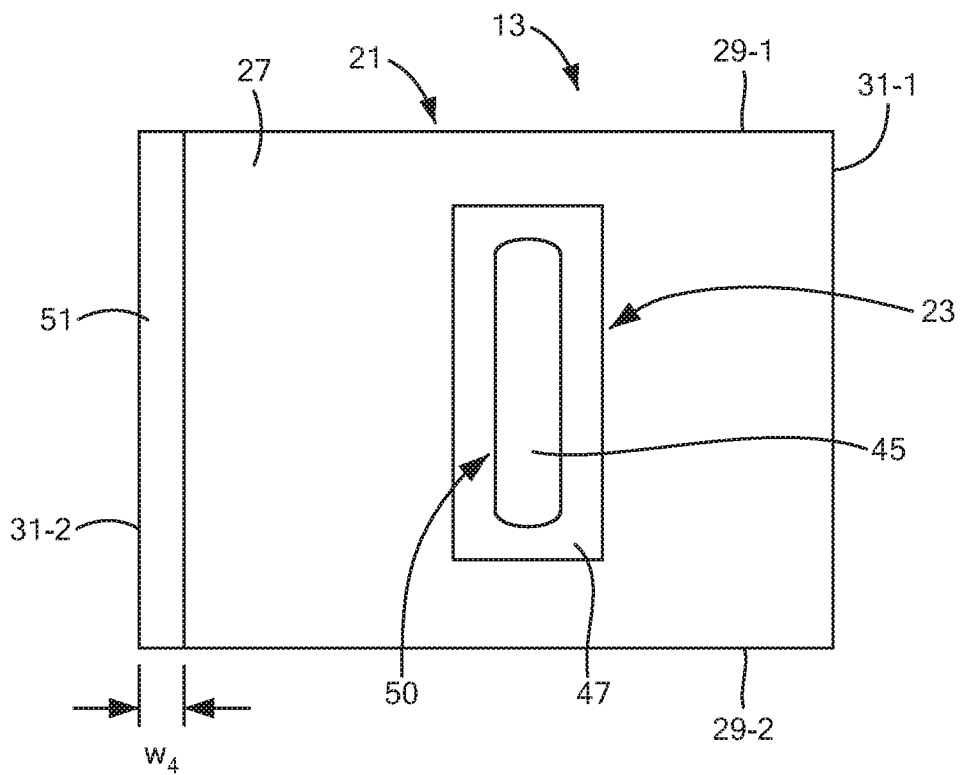
Figure 2C:
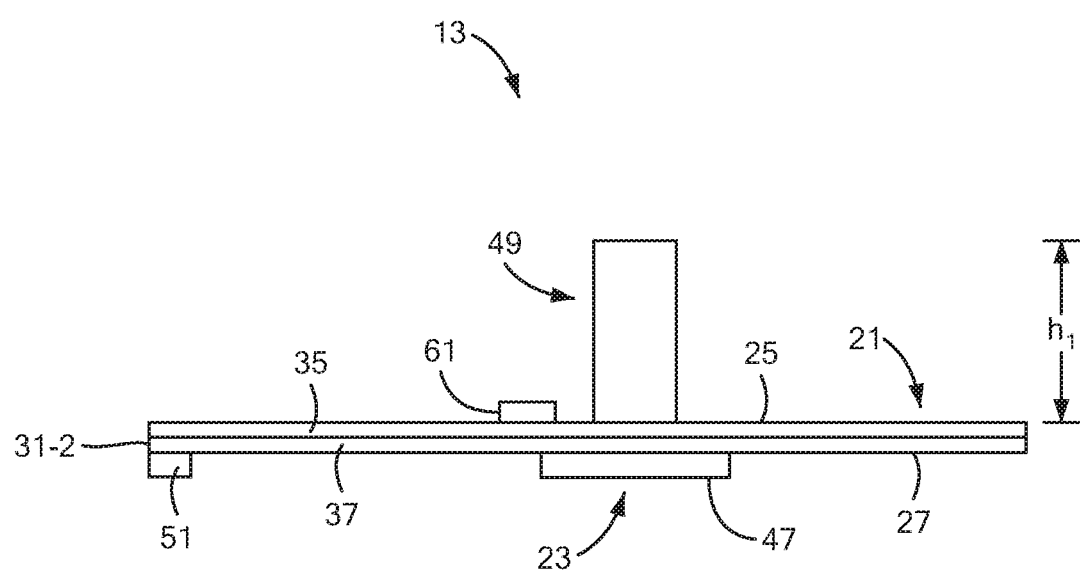

First drape 13, which is also shown in FIGS. 2(a) through 2(c), may comprise a first member 21 and a second member 23. (For clarity, certain details of first drape 13 that are discussed elsewhere in this application or that are not critical to an understanding of the invention may not be shown in all of FIG. 2(a) through 2(c) or may be shown therein in a simplified manner.) First member 21, which may be a planar yet flexible structure of generally rectangular shape, may be shaped to include a top surface 25, a bottom surface 27, a pair of sides 29-1 and 29-2, and a pair of ends 31-1 and 31-2. A transverse opening 33 may be provided in first member 21. Opening 33 may be generally rectangular in shape with slightly rounded ends. Opening 33 may extend generally parallel to ends 31-1 and 31-2, may be substantially centered relative to sides 29-1 and 29-2, and may be slightly off-center so as to be closer to end 31-1 than to end 31-2. The positioning of the opening 33 corresponds to the positioning of the paddle mount of the prone biopsy system and therefore could be shaped or positioned in other ways as to correspond to the geometries of the biopsy system.

First member 21, which may be used as a flexible cover or mat, may comprise one or more layers of material. In the present embodiment, first member 21 may comprise a first layer 35 and a second layer 37, first layer 35 being positioned over second layer 37. First layer 35 may comprise an absorbent material and, more specifically, may comprise a sheet of nonwoven hydrophilic/absorbent fabric comprising a natural or synthetic fiber. For example, first layer 35 may consist of or comprise a sheet of air-laid paper. If increased absorbency is desired, first layer 35 may further comprise a superabsorbent polymer, such as a polyacrylate. Second layer 37 may comprise a liquid-impervious material and, more specifically, may comprise a liquid-barrier plastic film or sheet. For example, second layer 37 may consist of or comprise a polyethylene film. First layer 35 and second layer 37 may have matching footprints and may be laminated to one another, either with or without an adhesive, or may otherwise be secured to one another by other suitable means. An illustrative example of a material suitable for use as first member 21 may include BEAUTIFUL LF20089 nonwoven laminate (Beautiful Nonwoven Co. Ltd., Nanhai Foshan City, China), which is a laminate of 110 gsm air-laid paper and a 25 gsm polyethylene film. An advantage of the two-layer structure is the dual nature of the first member 21. First, the absorbent first layer 35 serves to absorb fluid, while the second layer 37 provides liquid-resistant protection. Both are used to protect the biopsy apparatus from damage or contamination by bodily fluid.

Second member 23, which may comprise a unitary (i.e., one-piece) structure or which may comprise a plurality of structures that are joined together, may be shaped to include a pair of side walls 41-1 and 41-2, a pair of end walls 43-1 and 43-2, a top wall 45, and an outwardly-extending peripheral flange 47. Side walls 41-1 and 41-2, end walls 43-1 and 43-2, and top wall 45 may collectively define a protuberance 49, protuberance 49 extending upwardly relative to first member 21. Protuberance 49 may be hollow and may have a bottom opening 50, with peripheral flange 47 surrounding bottom opening 50. Protuberance 49 may extend upwardly through opening 33 of first member 21 and may be closely dimensioned to opening 33. Peripheral flange 47, which may be used to couple the entire perimeter of protuberance 49 to first member 21, may be secured to bottom surface 27 of first member 21. In the present embodiment, peripheral flange 47 is dimensioned to be secured only to a small portion of bottom surface 27 of first member 21, namely, the portion of bottom surface 27 that surrounds opening 33; however, alternatively, peripheral flange 47 may be dimensioned to be secured to a larger portion of bottom surface 27 of first member 21 and may be dimensioned to be secured to the entirety or substantially the entirety of bottom surface 27. Preferably, peripheral flange 47 is secured to bottom surface 27 of first member 21 in such a way as to form a water-tight seal therewith. For example, second layer 37 of first member 21 and second member 23 may be made of one or more materials that enable peripheral flange 47 to be heat-sealed to second layer 37 of first member 21 to form a water-tight seal therewith. Alternatively, in another embodiment (not shown), an additional bonding member and/or an additional sealing member may be used to bond peripheral flange 47 to first member 21 and/or to create a water-tight seal therebetween.

As will be discussed further below, protuberance 49 may be used to cover a paddle mount of a prone biopsy system, such as, but not limited to, the paddle mount of the AFFIRM® prone biopsy system. Accordingly, protuberance 49 is preferably appropriately dimensioned to receive at least the top of the paddle mount, as well as a significant portion of the sides of the paddle mount. Preferably, protuberance 49 is dimensioned purposefully to correspond generally to the size of the paddle mount, rather than having a much larger volume than the paddle mount. In this manner, the amount of absorbing surface area of first member 21 may be maximized. (For example, protuberance 49, which may extend perpendicularly relative to first member 21, may have a width that is substantially less than the length of first member 21 (e.g., as small as approximately one-tenth) and may have a length that is substantially less than the width of first member 21 (e.g., as small as approximately one-half).) In addition, by having protuberance 49 correspond generally to the size of the paddle mount, any adverse impact on the mounting of a paddle to a paddle mount covered by protuberance 49, as well as any interference with the Hall-effect sensors in the paddle mount, both of which may be caused by the "bunching" of excess material of protuberance 49, may be minimized. (It is to be understood that, whereas, in the present embodiment, protuberance 49 has a generally rectangular prismatic shape, protuberance 49 need not have such a shape.) Protuberance 49 is preferably made of a material that does not physically obstruct or impede the mounting of a compression paddle to the covered paddle mount and that does not interfere with or adversely impact the operation of the sensing mechanism, within the covered paddle mount, for detecting the type of compression paddle mounted on the paddle mount. As such, second member 23 may be made of a thin, flexible material, which is also preferably optically transparent or translucent to facilitate the mounting of the compression paddle on the covered paddle mount. Such a material may be, but not is not limited to, a clear polyethylene film, such as 2 mil clear polyethylene film.

First drape 13 may further comprise a fastener that may be used to couple first member 21 to a desired portion of a medical apparatus. In the present embodiment, such a fastener may comprise a strip of double-sided adhesive tape 51. One side of tape 51 may comprise a permanent adhesive that may face towards and be secured to first member 21, and the opposite side of tape 51 may comprise a removable adhesive that may face towards and be secured to a desired portion of the medical apparatus. (If desired, a peelable release paper (not shown) may be used to cover the removable adhesive prior to its deployment.) Tape 51 may be mounted on bottom surface 27 of first member 21, may be positioned substantially flush with or spaced inwardly a short distance from end 31-2, and may extend for a portion of or substantially the entire length of end 31-2. Examples of materials suitable for use in forming tape 51 may include, but are not limited to, 3M™ 9415 removable repositionable tape and 3M 856 polyester film tape, both of which are commercially available from 3M Company, Maplewood, Minn. The placement of the tape 51 allows for securing the first member 21 to the biopsy apparatus and preventing movement of the first drape 13 during the procedure, while leaving a portion of the first member 21 to be unsecured. The unsecured portion of the first member 21 can then freely fold, as described below, when the paddle moves to perform a breast compression.

First drape 13 may further comprise a layer of absorbent material 61. Layer 61, which may be mounted on top of first layer 35 of first member 21, may comprise an absorbent material that is more absorbent than the absorbent material of first layer 35 of first member 21. For example, layer 61 may comprise a sheet of nonwoven hydrophilic/absorbent fabric that is embedded with particles of a superabsorbent polymer, such as a polyacrylate, whereas first layer 35 may lack such a superabsorbent polymer. Alternatively, layer 61 may be similar in composition and/or absorbency to the absorbent material of first layer 35 of first member 21 but may simply provide an additional layer of absorbent material. In the present embodiment, layer 61 is shown as covering only a portion of first layer 35 and, in particular, is shown as a strip positioned parallel to and proximate to opening 33. More specifically, in the present embodiment, layer 61 may have a length and a width that is comparable to or slightly decreased relative to opening, with layer 61 being positioned to the side of opening 33 that faces end 31-2, as opposed to end 31-1. Nevertheless, it is to be understood that layer 61 could cover more of the surface area of layer 35 and, in fact, could cover substantially the entirety of layer 35. Layer 61 may be permanently secured to first layer 35 of first member 21 by stitching or by other suitable means. Alternatively, layer 61 may be removably mounted on first layer 35. As will be discussed further below, layer 61 may function to provide increased absorbency in the area below a compressed breast.

Preferably, first drape 13 is appropriately dimensioned so that, when used with a prone biopsy system like the AFFIRM® prone biopsy system, protuberance 49 may be inserted over the paddle mount, and first member 21 may extend from the paddle mount generally horizontally along the top of the platform on which the paddle mount is slidably mounted and then may extend generally vertically along the breast support platform, with end 31-2 of first member 21 being adhered to the breast support platform at a height just below the x-ray energy receptor. In this manner, when a breast is compressed between the compression paddle and the breast support platform, first member 21 may form one or more folds under the compressed breast. Such folds may increase the amount of surface area that is available to absorb fluid that may be emitted from the breast due to biopsy. In addition, layer 61 is preferably dimensioned and positioned on first member 21 so that, when a breast is compressed, layer 61 is positioned below the compressed breast, thereby providing additional absorbency. Also, first member 21 is preferably dimensioned to have a width that substantially covers the width of the platform on which the paddle mount is slidably mounted, as well as covering the width of the breast support platform. Finally, as is the case in the present embodiment, first drape 13 may be symmetric about its longitudinal centerline.

Along the foregoing lines, without wishing to be limited to any particular dimensions for first drape 13, exemplary dimensions for first drape 13 may be as follows: First member 21 may have a length $l_1$ of approximately 23.0 inches and a width $w_1$ of approximately 17.0 inches. Opening 33 may have a length $l_2$ of approximately 9.7 inches and a width $w_2$ of approximately 2.3 inches and may be spaced approximately 9.0 inches inwardly from end 31-1. Protuberance 49 may have a length $l_3$ of approximately 9.25 inches, a width $w_3$ of approximately 2.25 inches, and a height $h_1$ of approximately 4.5 inches. Tape 51 may have a width $w_4$ of 0.50 inch and may extend the entire length of end 31-2.

Figure 3A:
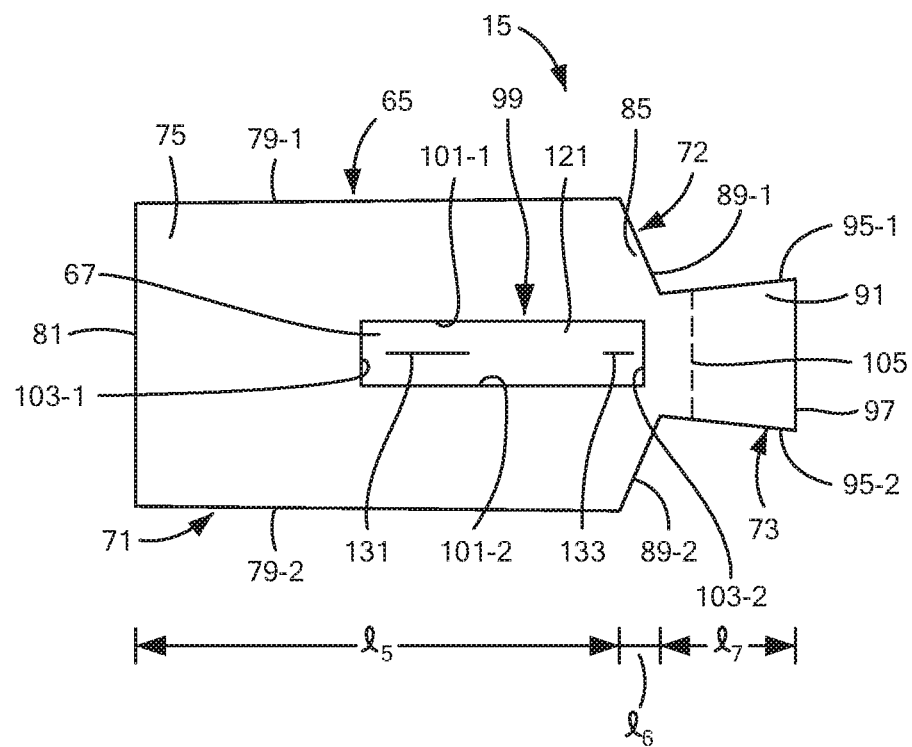
FIGS. 3(a) through 3(c) are top, bottom, and side views, respectively, of the second drape shown in FIG. 1.
Figure 3B:
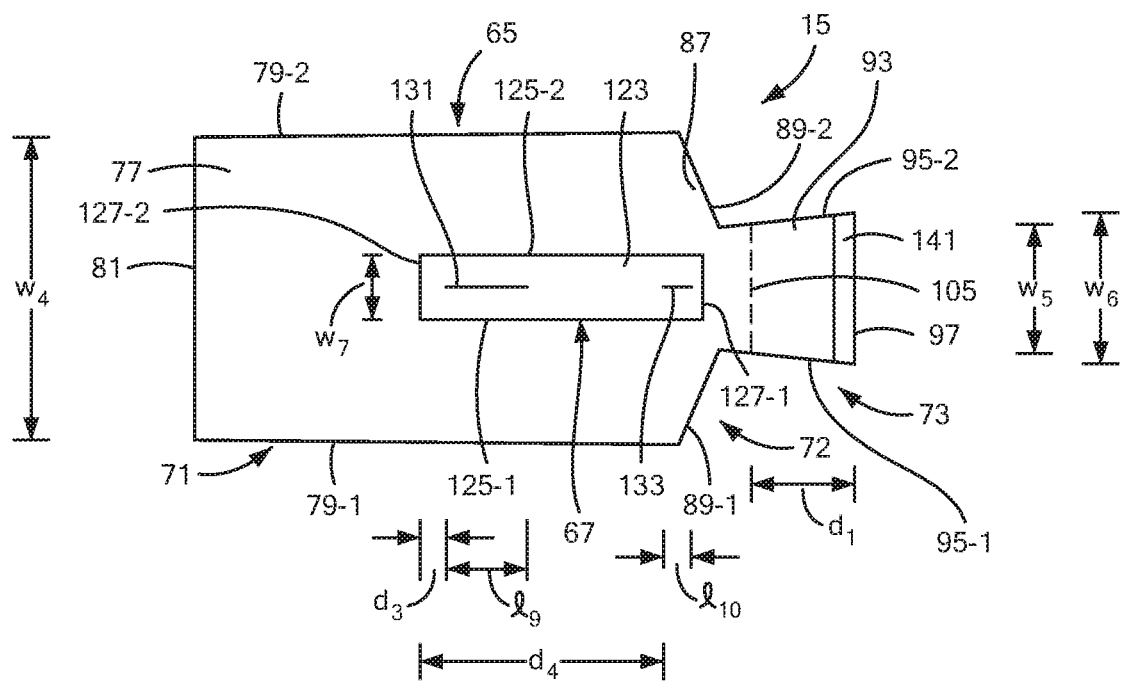
Figure 3C:
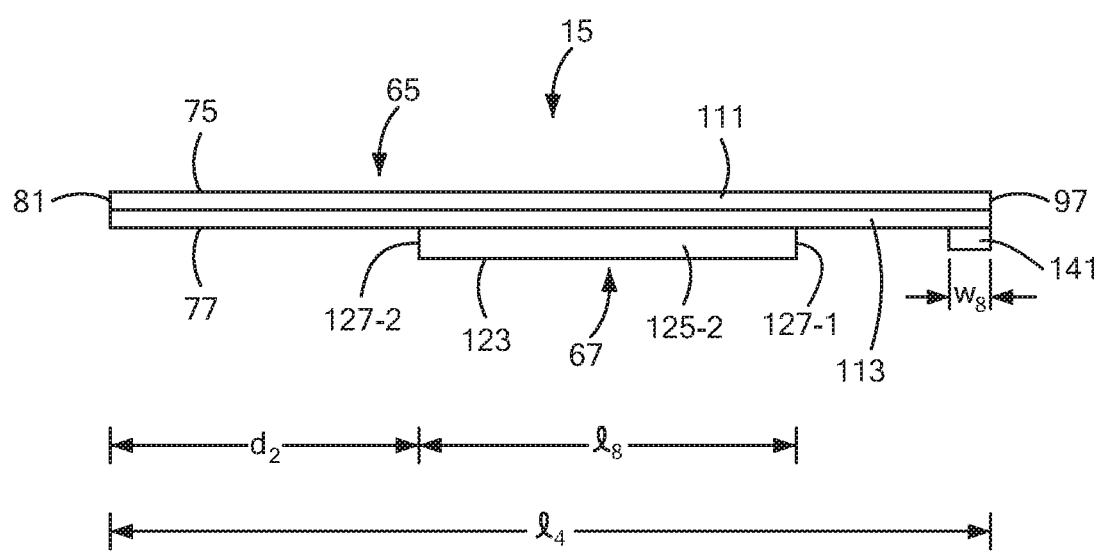

Second drape 15, which is also shown in FIGS. 3(*a*) through 3(*c*), may be used to cover the biopsy gun mount that is part of a prone biopsy system like the AFFIRM® prone biopsy system. During a biopsy procedure, bodily fluid, namely blood, can travel down the needle and the biopsy gun toward the gun mount. While the biopsy gun is removable and disposable, the remaining portions of the gun mount may be contaminated with bodily fluid. The second drape may comprise a first part 65 and a second part 67. (For clarity, certain details of second drape 15 that are discussed elsewhere in this application or that are not critical to an understanding of the invention may not be shown in all of FIG. 3(*a*) through 3(*c*) or may be shown therein in a simplified manner.) First part 65 may comprise a planar yet flexible structure comprising a first portion 71, a second portion 72, and a third portion 73, wherein second portion 72 may be intermediate to and may interconnect first portion 71 and third portion 73. First portion 71, which may be of generally rectangular shape, may be shaped to include a top surface 75, a bottom surface 77, a pair of sides 79-1 and 79-2, and a first end 81. Sides 79-1 and 79-2 may be parallel to one another, and each of sides 79-1 and 79-2 may be perpendicular to first end 81. Second portion 72 may be generally trapezoidal in shape and may be positioned at the end of first portion 71 that is opposite to first end 81. Second portion 72 may be shaped to include a top surface 85, a bottom surface 87, and a pair of inwardly-sloping sides 89-1 and 89-2. Third portion 73 may be generally trapezoidal in shape and may be positioned at the end of second portion 72 that is opposite to first portion 71. Third portion 73 may be shaped to include a top surface 91, a bottom surface 93, a pair of outwardly-sloping sides 95-1 and 95-2, and an end 97.

A transverse opening 99 may be provided in first part 65. Opening 99, which may be generally rectangular in shape, may be defined by a pair of sides 101-1 and 101-2 and a pair of ends 103-1 and 103-2. Sides 101-1 and 101-2 may extend generally parallel to sides 79-1 and 79-2, and opening 99 may be substantially centered relative to sides 79-1 and 79-2. End 103-1 may be positioned in first portion 71 and may be slightly closer to end 81 than to second portion 72. End 103-2 may be positioned in second portion 72 and may be proximate to the interface of second portion 72 and third portion 73.

One or more perforations 105 may be provided in first part 65. Perforations 105 may be positioned in third portion 73 and may be arranged to extend between sides 95-1 and 95-2. Perforations 105 may be spaced a short distance from the interface of second portion 72 and third portion 73. As will be discussed further below, perforations 105 may be used to detach a distal portion of third portion 73 from the remainder of first part 65.

First part 65, which may function as a flexible cover or mat, may comprise one or more layers of material. In the present embodiment, first part 65 may comprise a first layer 111 and a second layer 113, first layer 111 being positioned over second layer 113. First layer 111 may comprise an absorbent material and, more specifically, may comprise a sheet of nonwoven hydrophilic/absorbent fabric comprising a natural or synthetic fiber. For example, first layer 111 may consist of or comprise a sheet of air-laid paper. If increased absorbency is desired, first layer 35 may further comprise a superabsorbent polymer, such as a polyacrylate. Second layer 113 may comprise a liquid-impervious material and, more specifically, may comprise a liquid-barrier plastic film or sheet. For example, second layer 113 may consist of or comprise a polyethylene film. First layer 111 and second layer 113 may have matching footprints and may be laminated to one another, either with or without an adhesive, or may otherwise be secured to one another by other suitable means. An illustrative example of a material suitable for use as first part 65 may include BEAUTIFUL LF20089 nonwoven laminate (Beautiful Nonwoven Co. Ltd., Nanhai Foshan City, China), which is a laminate of 110 gsm air-laid paper and a 25 gsm polyethylene film.

Second part 67 of second drape 15, which may comprise a unitary planar structure, may be shaped to include a top 121, a bottom 123, a pair of sides 125-1 and 125-2, and a pair of ends 127-1 and 127-2. Second part 67 may be of generally rectangular shape and may be appropriately dimensioned to be slightly longer and slightly wider than opening 99. Second part 67 may be disposed below first part 65 and may be positioned relative to first part 65 so that opening 99 is substantially centered relative to top 121. The periphery of top 121 may be secured to corresponding areas of bottom surface 77 of first portion 71 and to bottom surface 87 of second portion 72 by an adhesive (not shown) or by other suitable means. In particular, the periphery of second part 67 may be secured to first part 65 in a water-tight fashion. Preferably, second part 67 comprises an elastic material, an example of which may be a Kraton™ film having a thickness of approximately 5 mil. The use of an elastic material in second part 67 may enable second drape 15 to provide improved coverage over portions of a medical apparatus lying thereunder, particularly when the medical apparatus is in use.

One or more longitudinally-extending transverse slits may be provided in second part 67. Said one or more slits may include a first slit 131 and a second slit 133. Each of first slit 131 and second slit 133 may be positioned along the centerline of second part 67. First slit 131 may be positioned proximate to and spaced inwardly from end 127-2, and second slit 133 may be positioned proximate to and spaced inwardly from end 127-1. First slit 131 may be longer than second slit 133 and may be appropriately dimensioned and positioned to enable the insertion therethrough of the gun mount of a medical apparatus like the AFFIRM® prone biopsy system. Second slit 133 may be appropriately dimensioned and positioned to enable the insertion therethrough of the needle guide of a medical apparatus like the AFFIRM® prone biopsy system.

Second drape 15 may further comprise a fastener that may be used to couple first part 65 of second drape 15 to a desired portion of a medical apparatus. In the present embodiment, such a fastener may comprise a strip of double-sided adhesive tape 141. One side of tape 141 may comprise a permanent adhesive that may face towards and be secured to first part 65, and the opposite side of tape 141 may comprise a removable adhesive that may face towards and be secured to a desired portion of the medical apparatus. (If desired, a peelable release paper (not shown) may be used to cover the removable adhesive prior to its deployment.) Tape 141 may be mounted on bottom surface 93 of third portion 73 of first part 65, may be positioned substantially flush with or spaced inwardly a short distance from end 97, and may extend for a portion of or substantially the entire distance between sides 95-1 and 95-2. Examples of materials suitable for use in forming tape 141 may include, but are not limited to, 3M™ 9415 removable repositionable tape and 3M 856 polyester film tape, both of which are commercially available from 3M Company, Maplewood, Minn.

Preferably, second drape 15 is appropriately dimensioned so that, when used with a prone biopsy system like the AFFIRM® prone biopsy system, the gun mount may be inserted through first slit 131, the needle guide may be inserted through second slit 133, and end 97 of third portion 73 may be adhered via tape 141 over the base of the compression paddle. In addition, second drape 15 preferably has a length and a width to substantially cover the slide carriage assembly and several other components of the slide arm assembly. Finally, as is the case in the present embodiment, second drape 15 may be symmetric about its longitudinal centerline.

Along the foregoing lines, without wishing to be limited to any particular dimensions for second drape 15, exemplary dimensions for second drape 15 may be as follows: First part 65 may have an overall length $l_4$ of approximately 28.5 inches and a maximum width $w_4$ of approximately 13.0 inches. More specifically, first portion 71 may have a length $l_5$ of approximately 21.0 inches, second portion 72 may have a length $l_6$ of approximately 1.5 inches and a minimum width $w_5$ of approximately 5.0 inches, and third portion 73 may have a length $l_7$ of 6.0 inches and a maximum width $w_6$ of approximately 6.0 inches. Perforations 105 may be spaced from end 97 by a distance $d_1$ of 4.5 inches. Second part 67 may have a length $l_8$ of approximately 12.8 inches and a width $w_7$ of approximately 3.8 inches. Second part 67 may be spaced from end 81 by a distance $d_2$ of approximately 9.6 inches. Slit 131 may have a length $l_9$ of approximately 3.1 inches and may be spaced from end 127-2 by a distance $d_3$ of approximately 1.4 inches. Slit 133 may have a length $l_{10}$ of approximately 1.3 inches and may be spaced from end 127-2 by a distance $d_4$ of approximately 10.8 inches. Tape 141 may have a width $w_8$ of 1.0 inch and may extend along the entire length of 97.

Figure 4A:
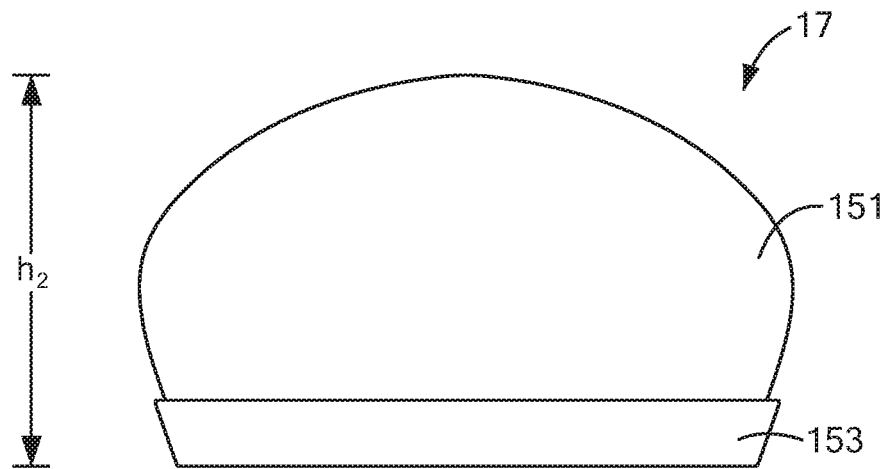
Figure 4B:
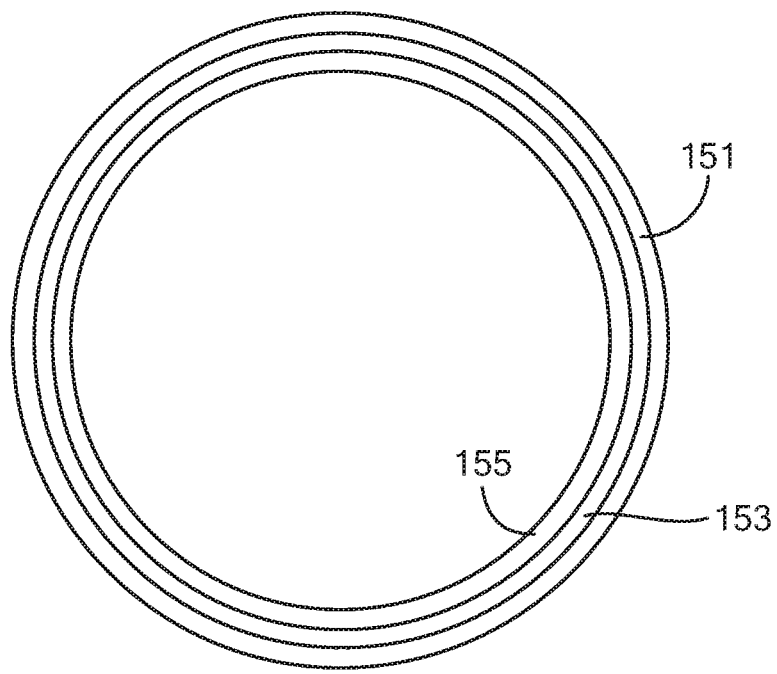

Third drape 17, which is also shown in FIGS. 4(a) and 4(b), may comprise a first component 151 and a second component 153. (For clarity, certain details of third drape 17 that are discussed elsewhere in this application or that are not critical to an understanding of the invention may not be shown in all of FIGS. 4(a) and 4(b) or may be shown therein in a simplified manner.) First component 151, which may comprise a unitary structure made of a flexible material, may be in the shape of a generally rounded pouch having an open bottom circumscribed by a peripheral rim 155. For reasons to become apparent below, first component 151 is preferably optically transparent. An example of a material suitable for use as first component 151 may be, but is not limited to, a clear polyethylene film, such as a clear polyethylene film having a thickness of approximately 1.5 mil.

Second component 153 of third drape 17, which may be circular in shape and which may comprise an elastic band or other resilient structure, may be secured by an adhesive (not shown) or other suitable means to first component 151, preferably by being secured around the exterior of peripheral rim 155. In this manner, second component 153 may serve to bias the open bottom of first component 151 to a reduced size. By contrast, to enlarge the size of the open bottom of first component 151, second component 153 may be stretched outwardly. Overall, third drape 17 may have a construction similar to a shower cap.

Preferably, third drape 17 is appropriately dimensioned so that, when used with a prone biopsy system like the AFFIRM® prone biopsy system, third drape 17 may be used to cover the control panel of the system. This may be done, for example, by stretching second component 153 sufficiently to permit peripheral rim 155 to be inserted over the control panel, then positioning first component 151 around the control member, and then releasing second component 153, whereby the control member may be substantially encapsulated by first component 151. In addition, first component 151 is preferably sufficiently thin to permit the control member to be seen and to be operated while first component 151 is positioned thereover.

Along the foregoing lines, without wishing to be limited to any particular dimensions for third drape 17, exemplary dimensions for third drape 17 may be as follows: First component 151 may have an overall height $h_2$ of approximately 3-4 inches. Second component 153 may be stretched to a maximum diameter of approximately 15 inches.

Figure 5A:
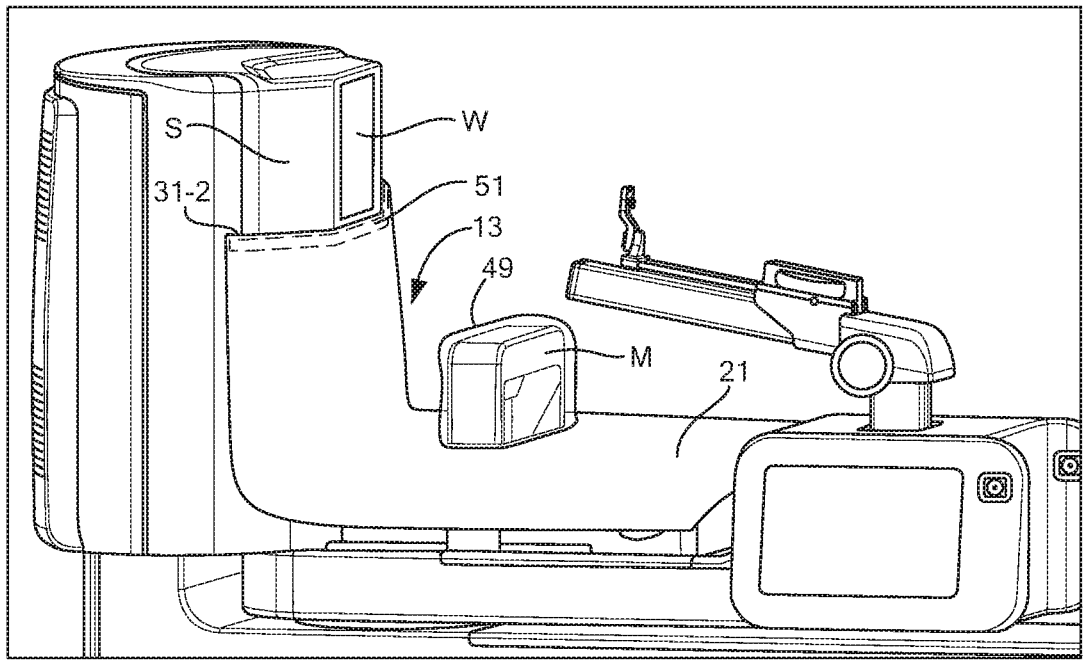
FIGS. 5(a) through 5(e) are simplified perspective views, showing one manner of installing the draping system of FIG. 1 on a prone biopsy system.
Figure 5B:
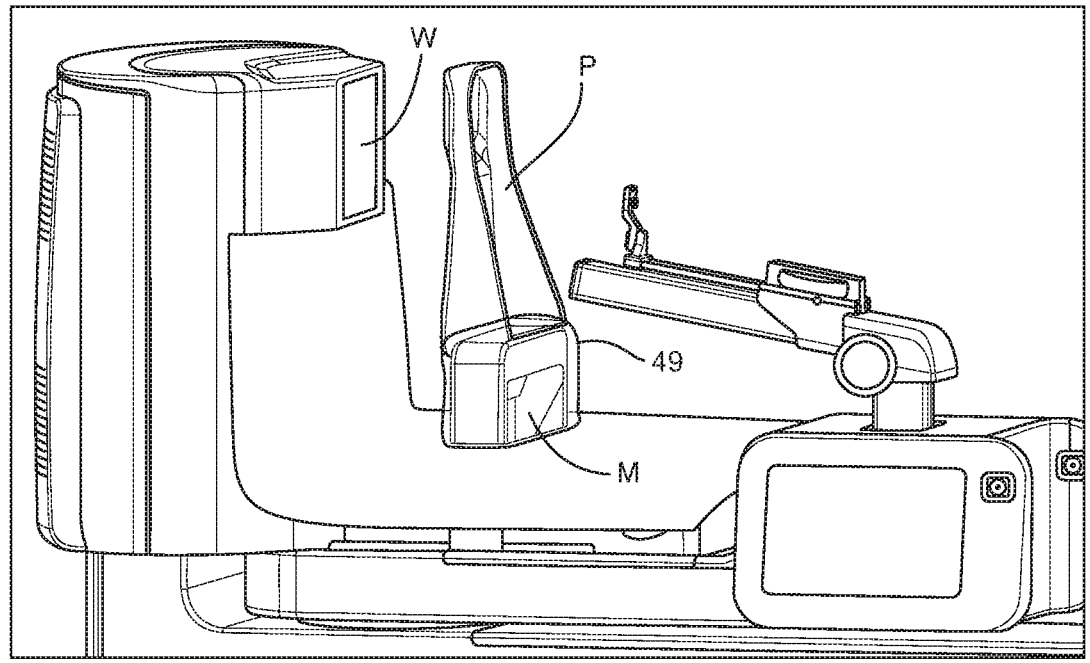
Figure 5C:
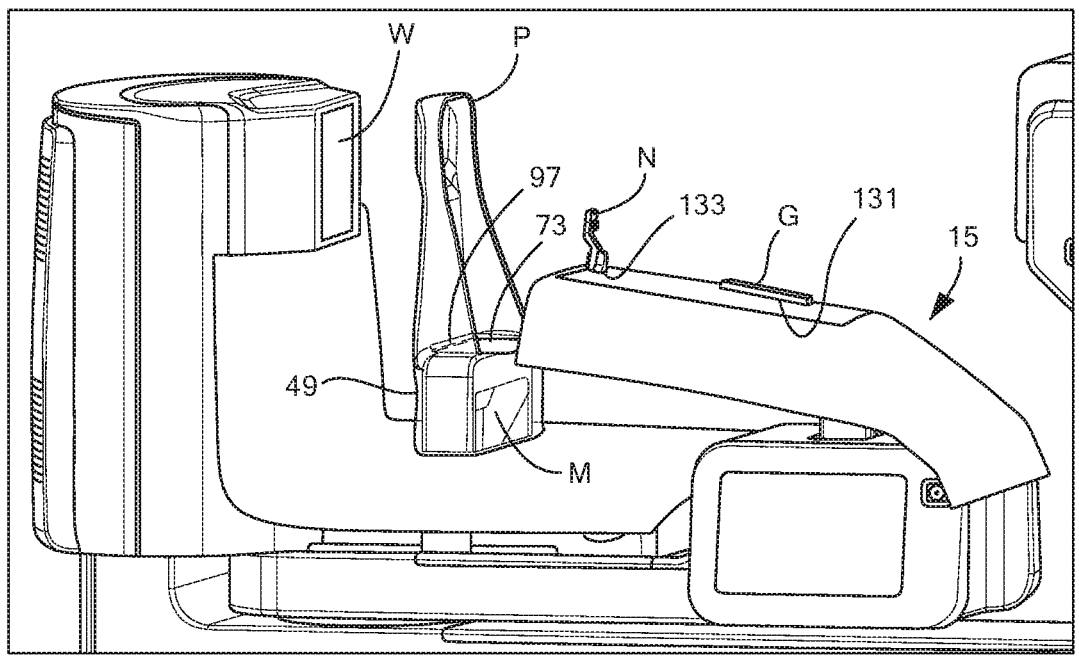
Figure 5D:
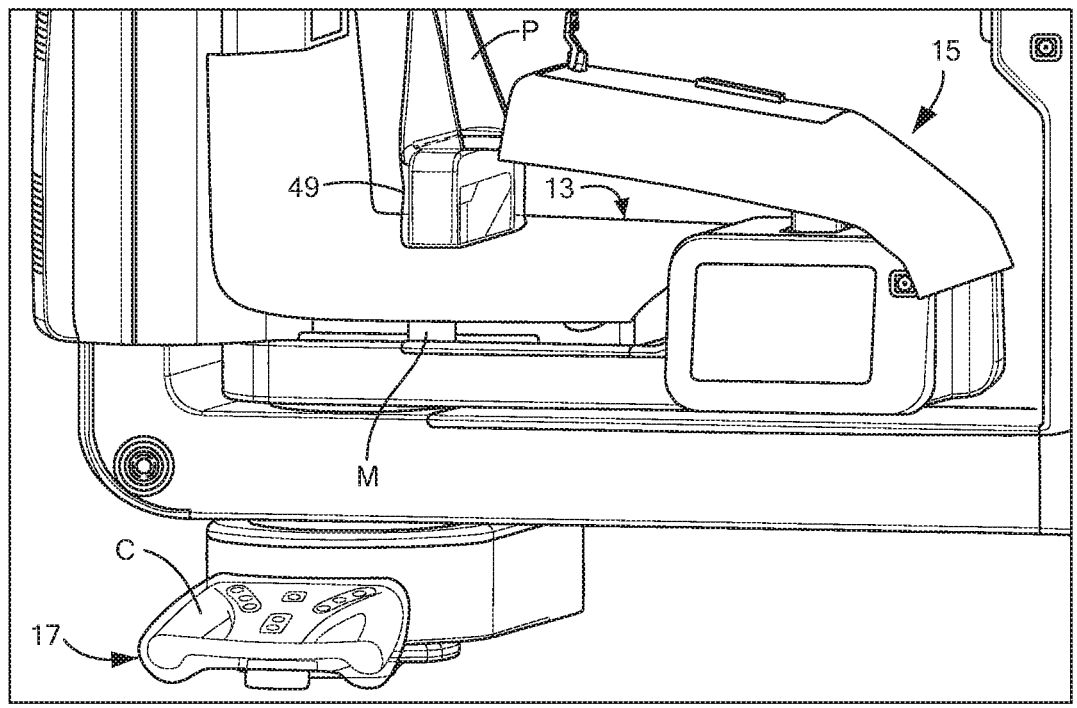
Figure 5E:
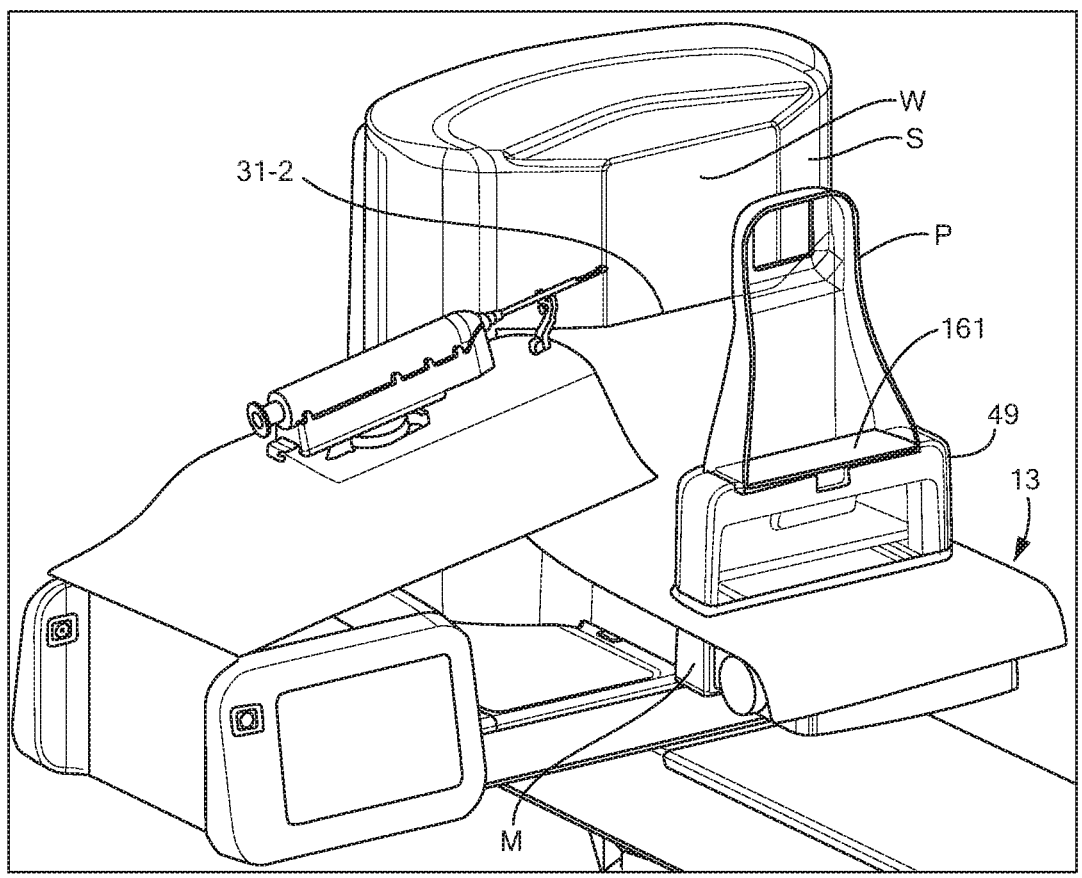

Referring now to FIGS. 5(a) through 5(e), there is shown one manner in which draping system 11 may be used in connection with a prone biopsy system, such as, but not limited to, the AFFIRM® prone biopsy system. (For ease of illustration, strip 61 is not shown in FIGS. 5(a) through 5(e). In addition, other details of draping system 11 that are not critical to an understanding of the invention may not be shown in all of FIG. 5(a) through 5(e) or may be shown therein in a simplified manner.) First, as can be seen in FIG. 5(a), first drape 13 may be installed by inserting protuberance 49 over a paddle mount M and by using tape 51 (shown in phantom) to secure end 31-2 of first member 21 to a breast support surface S just below a white square W that identifies the location of an x-ray receptor behind the breast support surface S. Next, as can be seen in FIG. 5(b), a compression paddle P may be mounted over protuberance 49 to paddle mount M. Because protuberance 49 is preferably thin-walled, flexible and transparent, the mounting of compression paddle P to paddle mount M is not impeded by protuberance 49. In addition, protuberance 49 preferably does not impede the ability of the sensing mechanism within paddle mount M from being able to identify the type of compression paddle P being mounted thereon. Next, as can be seen in FIG. 5(c), second drape 15 may be installed by inserting a gun mount G and a needle guide N through slits 131 and 133, respectively, and by using tape 141 (not shown) to secure end 97 of third portion 73 over the base of the compression paddle P. Next, as can be seen in FIG. 5(d), third drape 17 may be installed over a control panel C. Because first component 151 of third drape 17 is preferably thin-walled, flexible and transparent, the mounting of third drape 17 over control panel C does not impede an operator's ability to use control panel C. As noted above, the AFFIRM® prone biopsy system can be used in either an anterior-approach mode or a lateral-approach mode. As can be seen in FIG. 5(e), if used in a lateral-approach mode, third portion 73 of second drape 15 may be separated along perforations 105 into two pieces, with a distal piece 161 remaining on the base of compression paddle P.

Figure 6:
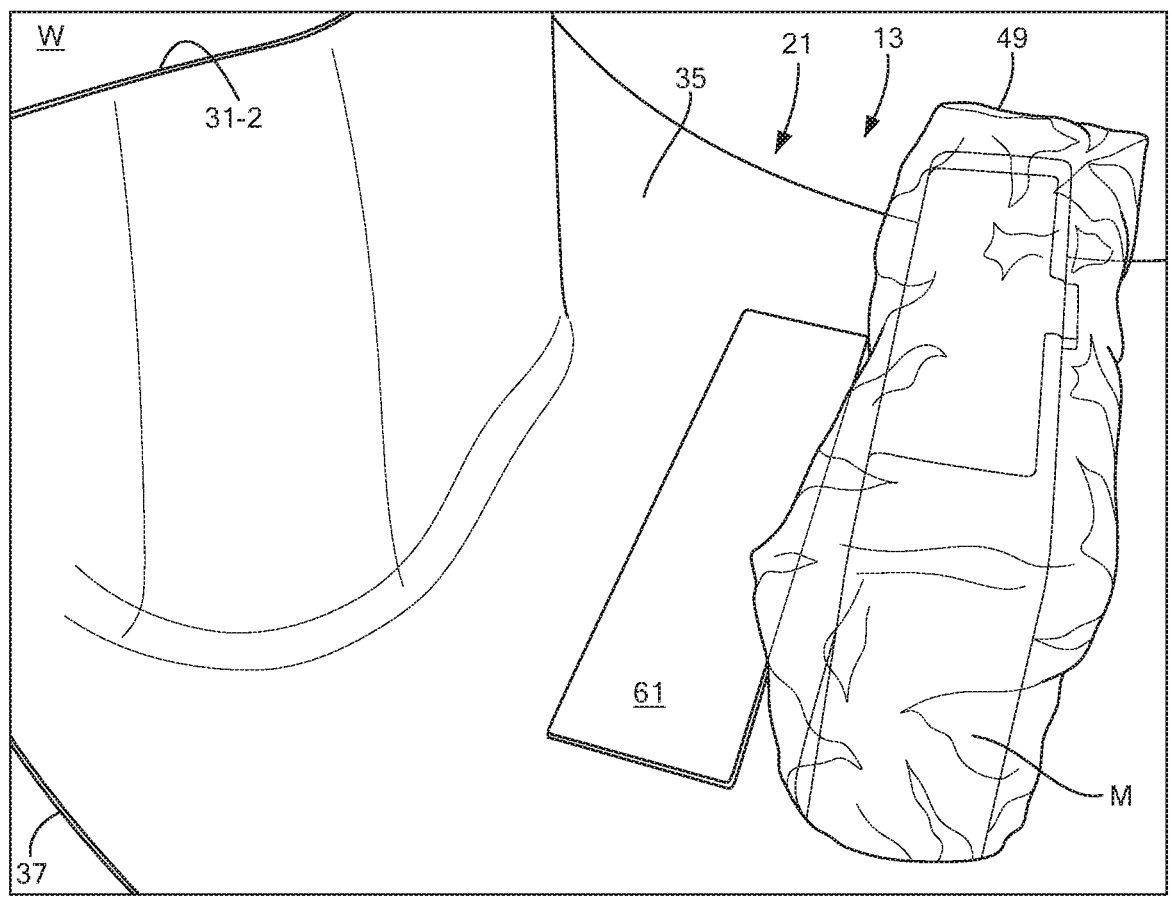
FIG. 6 is an image, showing the first drape installed on a prone biopsy system prior to the mounting of a compression paddle on the paddle mount.
Figure 7:
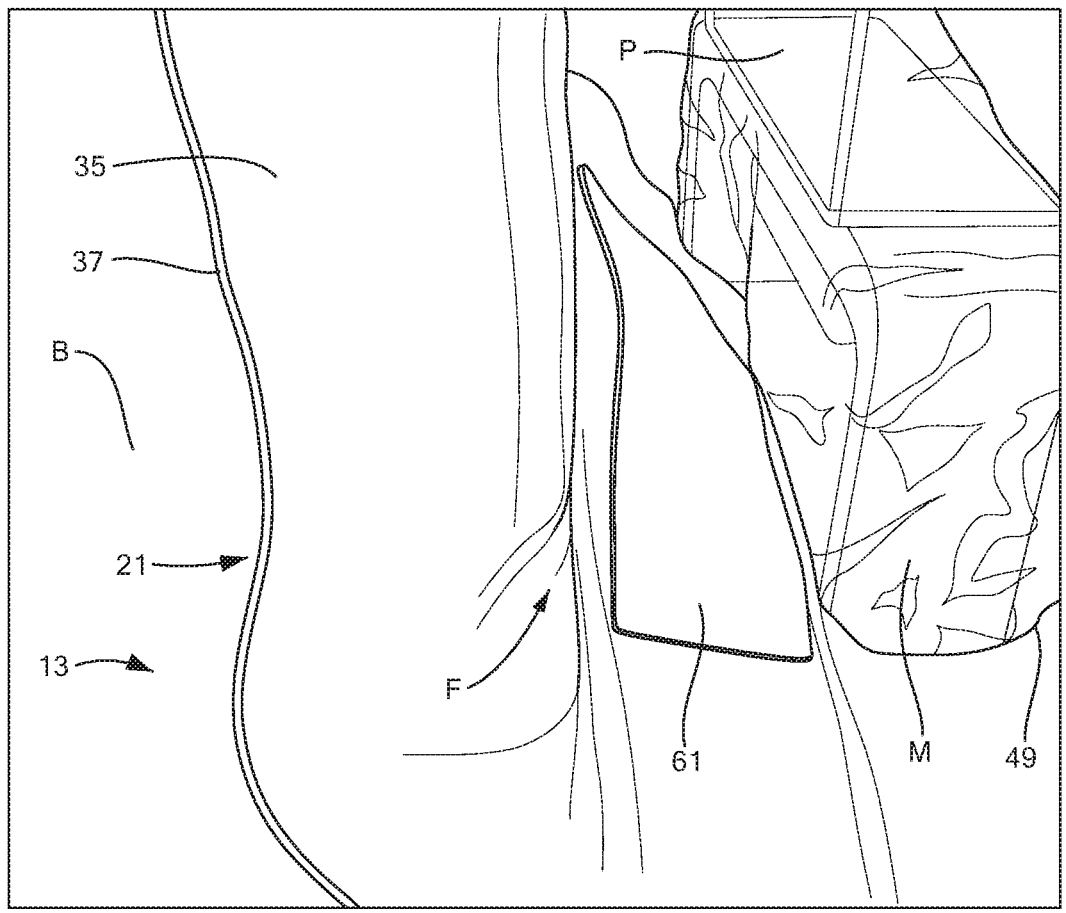
FIG. 7 is an image, showing the first drape installed on a prone biopsy system, the compression paddle mounted on the paddle mount, and the compression paddle placed in a compressed position.
Figure 8A:
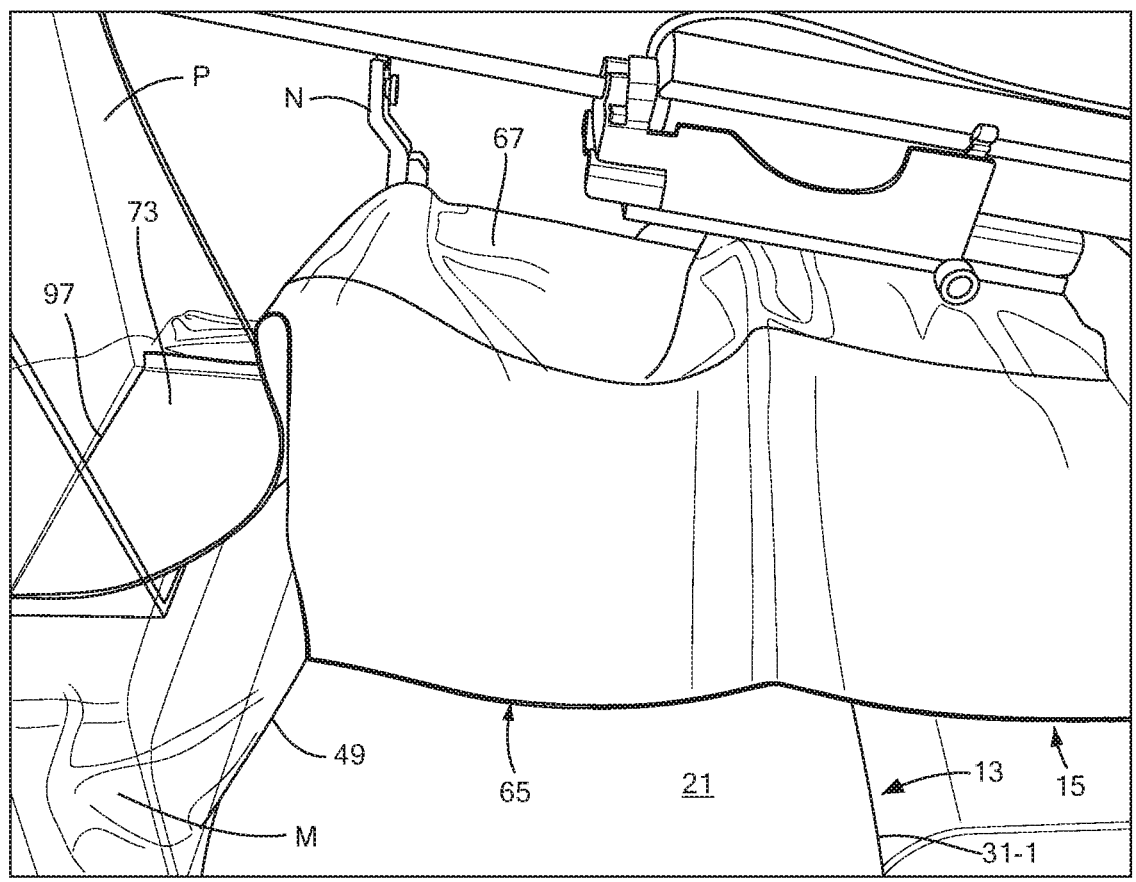
FIGS. 8(a) and 8(b) are images, showing the first drape and the second drape installed on a prone biopsy system.
Figure 8B:
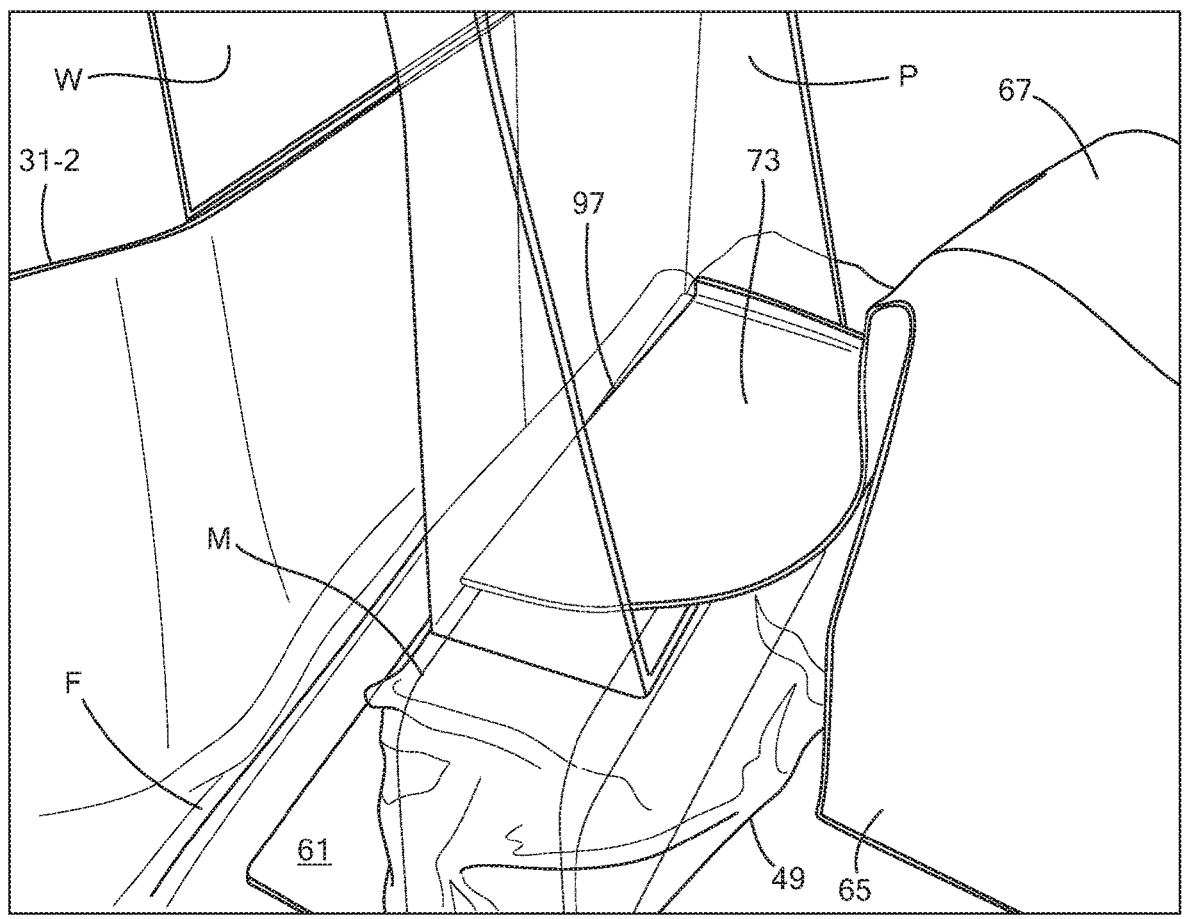

FIGS. 6, 7, 8(a) and 8(b) are additional images, showing components of draping system 11 installed on a prone biopsy system like the AFFIRM® prone biopsy system. More specifically, FIG. 6 is an image, showing first drape 13 installed prior to the mounting of a compression paddle on the paddle mount M. FIG. 7 is an image, showing first drape 13 installed, a compression paddle P mounted on the paddle mount M, and the combination of compression paddle P and paddle mount M moved to a breast compressing position. As can be seen, with compression paddle P and paddle mount M moved to a breast compressing position, one or more folds F are formed in first member 21 of first drape 13, and absorbent material 61 is positioned directly below where the compressed breast will be situated. Consequently, fluids emitted from the biopsied breast may be captured by the folds and/or absorbent material 61. FIGS. 8(a) and 8(b) are images, showing both first drape 13 and second drape 15 installed.

As can be appreciated, for purposes of transport and/or storage prior to use, first drape 13, second drape 15, and third drape 17 may be packaged together in a suitable container, such as a cardboard box.

Figure 9:
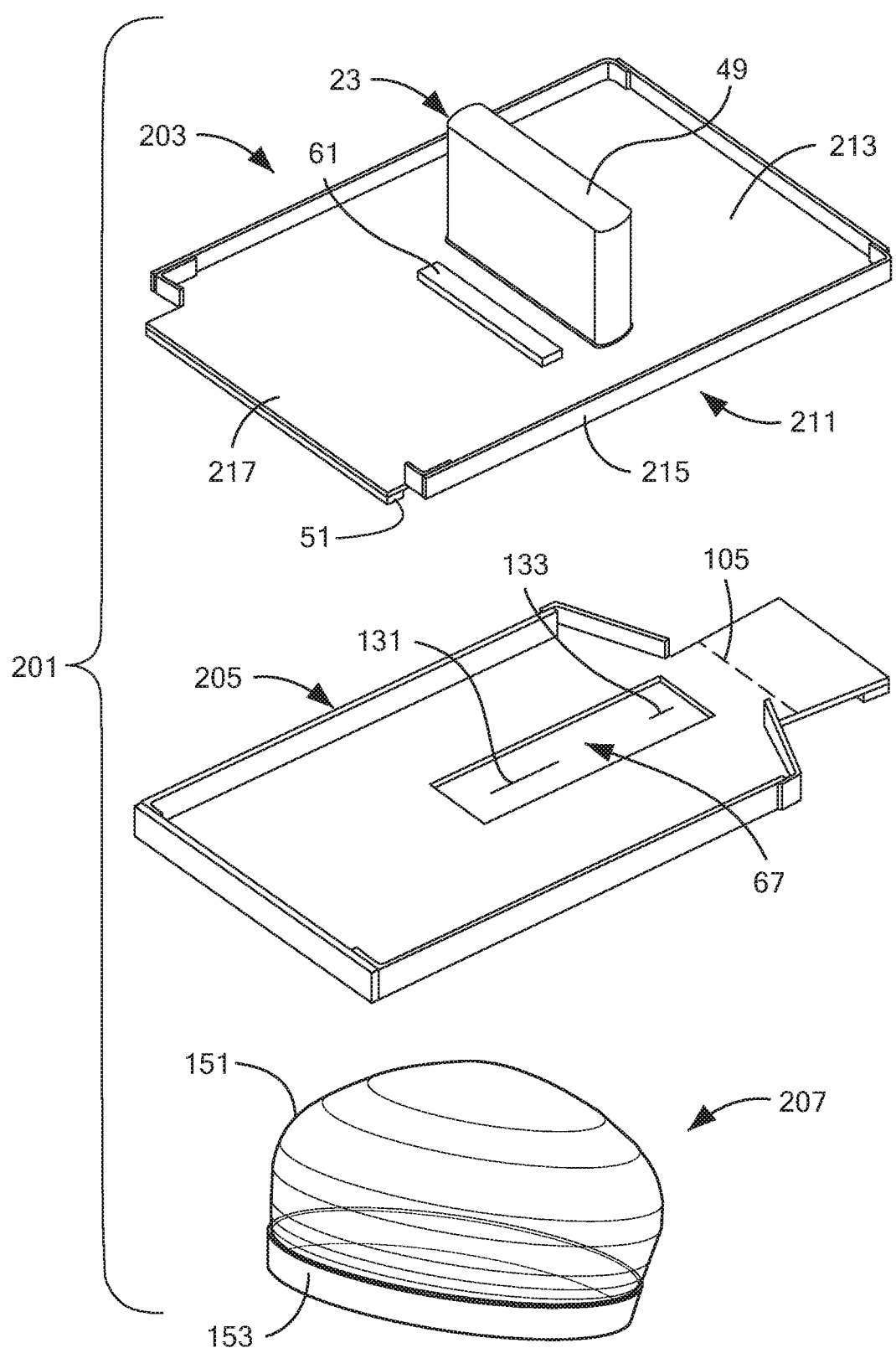
FIG. 9 is a perspective view of a second embodiment of a draping system that is suitable for use with a medical apparatus, in particular, a prone biopsy system, the draping system being constructed according to the present invention.

Referring now to FIG. 9, there is shown a perspective view of a second embodiment of a draping system that is suitable for use with a medical apparatus, in particular, a prone biopsy system, the draping system being constructed according to the present invention and being represented generally by reference numeral 201. For clarity, certain details of draping system 201 that are discussed elsewhere in this application or that are not critical to an understanding of the invention may not be shown in FIG. 9 or may be shown therein in a simplified manner.

Figure 10A:
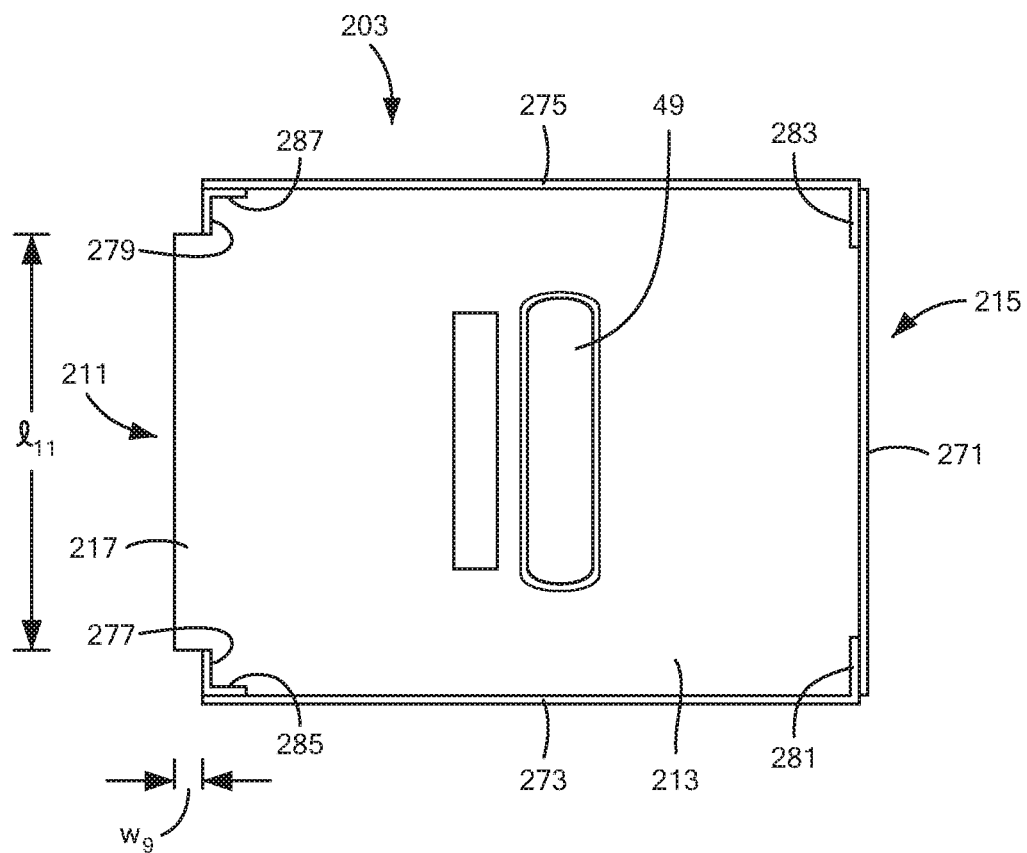
FIGS. 10(a) and 10(b) are top and side views, respectively, of the first drape shown in FIG. 9.
Figure 10B:
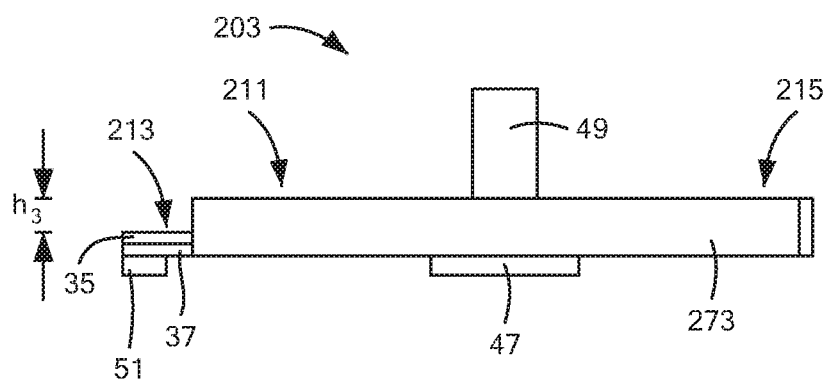

Draping system 201 may comprise a first drape 203, a second drape 205, and a third drape 207. First drape 203, which is also shown in FIGS. 10(a) and 10(b), may be similar in many respects to first drape 13. (For clarity, certain details of first drape 203 that are discussed elsewhere in this application or that are not critical to an understanding of the invention may not be shown in all of FIGS. 10(a) and 10(b) or may be shown therein in a simplified manner.) One difference between drape 203 and drape 13 may be that drape 203 may comprise a first member 211, instead of first member 21. First member 211 may be configured to comprise a mat portion 213, which may be a generally planar yet flexible structure, and a skirt portion 215, which may extend upwardly from mat portion 213 around at least a portion of the periphery of mat portion 213. Mat portion 213 may be configured similarly to first portion 21 of drape 13, except that mat portion 213 may be missing corner portions that correspond to those present at the extremities of end 31-2 of first portion 21. Skirt portion 215, which may surround all but a tab 217 at the distal end of mat 213, may be useful in keeping fluids from running over the sides and proximal end of mat portion 213, particularly where the flow rate of a fluid across mat portion 213 exceeds the absorbency rate of the fluid by mat portion 213. In the present embodiment, skirt portion 215 may have a height $h_3$ of approximately 1.0 inch, and tab 217 may have a length $l_{11}$ of approximately 14 inches and a width $w_9$ of approximately 1 inch.

Figure 11A:
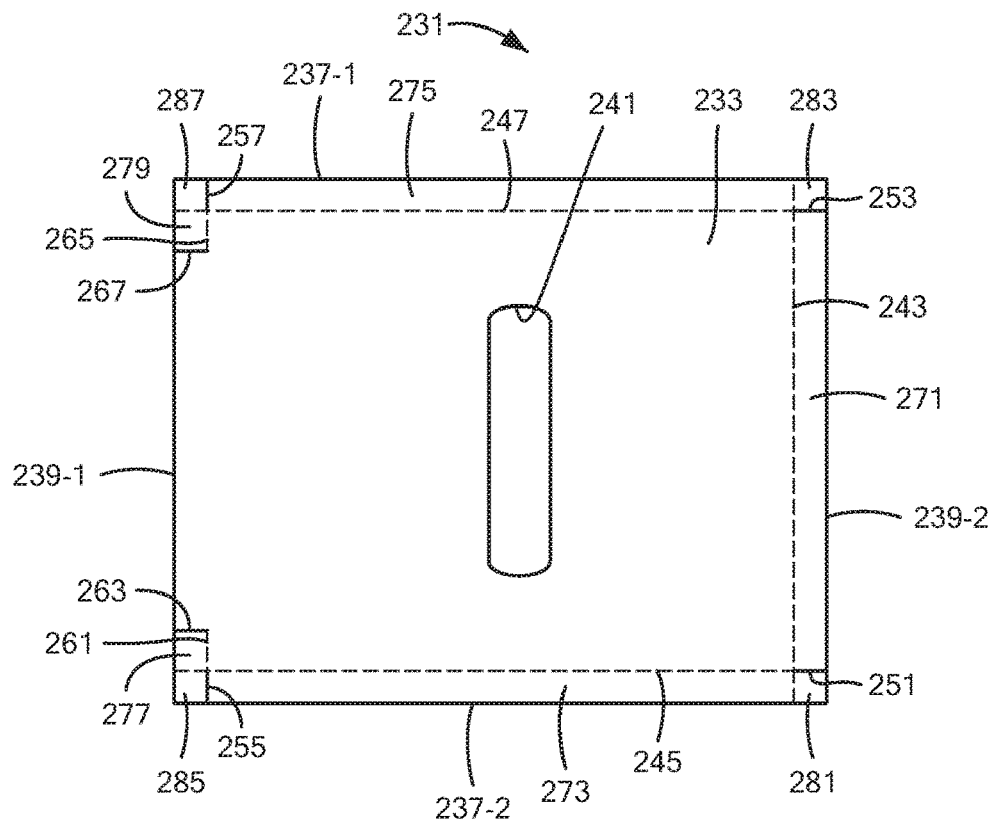
FIGS. 11(a) and 11(b) are top and bottom views, respectively, of a sheet that may be used to make the first member of the first drape of FIGS. 10(a) and 10(b)
Figure 11B:
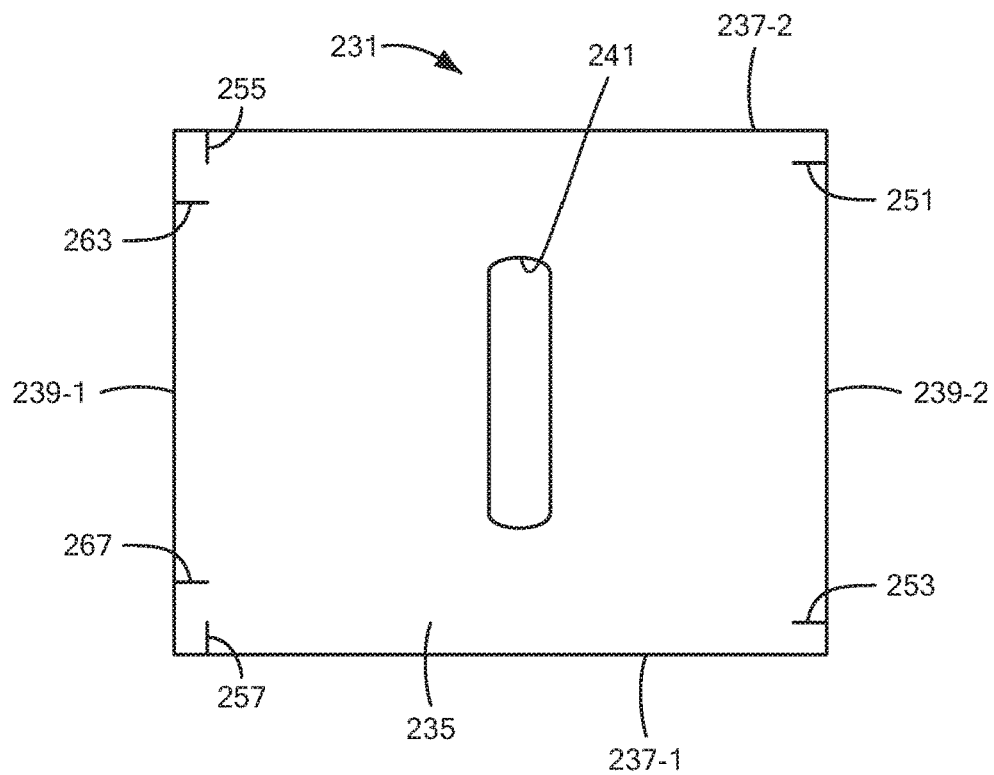

Referring now to FIGS. 11(a) and 11(b), there are shown top and bottom views, respectively, of a sheet that may be used to form first member 211, the sheet being represented generally by reference numeral 231. Sheet 231, which may be a laminated structure comprising two layers similar to layers 35 and 37 of first member 21, may be a generally rectangular structure comprising a top 233, a bottom 235, a pair of sides 237-1 and 237-2, and a pair of ends 239-1 and 239-2. A transverse opening 241, which may be similar to transverse opening 33 of first member 21, may be provided in sheet 231. A first fold line 243 (represented in FIG. 11(a) using dashed lines) may extend from side 237-1 to side 237-2 and may be parallel to and spaced a short distance inwardly from end 239-2. A second fold line 245 (represented in FIG. 11(a) using dashed lines) may extend from end 239-1 to first fold line 243 and may be parallel to and spaced a short distance inwardly from side 237-2. A third fold line 247 (represented in FIG. 11(a) using dashed lines) may extend from end 239-1 to first fold line 243 and may be parallel to and spaced a short distance inwardly from side 237-1. A first transverse cut 251 may extend from end 239-2 to first fold line 243 and may be aligned with second fold line 245. A second transverse cut 253 may extend from end 239-2 to first fold line 243 and may be aligned with third fold line 247. A third transverse cut 255 may extend from side 237-2 to first fold line 245 and may be parallel to and spaced a short distance inwardly from end 239-1. A fourth transverse cut 257 may extend from side 237-1 to second fold line 247 and may be parallel to and spaced a short distance inwardly from end 239-1. A fourth fold line 261 (represented in FIG. 11(a) using dashed lines) may be aligned with third transverse cut 255 and may extend a short distance inwardly therefrom. A fifth transverse cut 263 may extend from end 239-1 to the end of fourth fold line 261 that lies opposite to third transverse cut 255. A fifth fold line 265 (represented in FIG. 11(a) using dashed lines) may be aligned with fourth transverse cut 257 and may extend a short distance inwardly therefrom. A sixth transverse cut 267 may extend from end 239-1 to the end of fifth fold line 265 that lies opposite to fourth transverse cut 257. Sheet 231 may be scored along fold lines 243, 245, 247, 261 and 265 to facilitate the folding of sheet 231.

End 239-2, fold line 243, and cuts 251 and 253 may collectively be used to define a first panel 271. Side 237-2, fold lines 243 and 245, and cut 255 may collectively be used to define a second panel 273. Side 237-3, fold lines 243 and 247, and cut 257 may collectively be used to define a third panel 275. End 239-1, fold lines 245 and 261, and cut 263 may collectively be used to define a fourth panel 277. End 239-1, fold lines 247 and 265, and cut 267 may collectively be used to define a fifth panel 279. End 239-2, fold line 243, and cut 251 may collectively be used to define a tab 281. End 239-2, fold line 243, and cut 253 may collectively be used to define a tab 283. Side 237-2, fold line 245, and cut 255 may collectively be used to define a tab 285. Side 237-1, fold line 247, and cut 257 may collectively be used to define a tab 287.

To assemble first member 211 from sheet 231, one may fold sheet 231 along fold lines 243 and 245 and then may secure tab 281 to panel 271 using an adhesive (not shown) or other suitable securing means. Also, one may fold sheet 231 along fold line 247 and then may secure tab 283 to panel 271 using an adhesive (not shown) or other suitable securing means. In addition, one may fold sheet along fold line 261 and then may secure tab 285 to panel 273 using an adhesive (not shown) or other suitable securing means. Additionally, one may fold sheet 231 along fold line 279 and then may secure tab 287 to panel 275 using an adhesive (not shown) or other suitable securing means.

It is to be understood that, whereas, in the present embodiment, mat portion 213 and skirt portion 215 are integrally formed as a one-piece structure, mat portion 213 and skirt portion 215 need not form a unitary structure and may be constructed from two or more separate pieces.

Figure 12A:
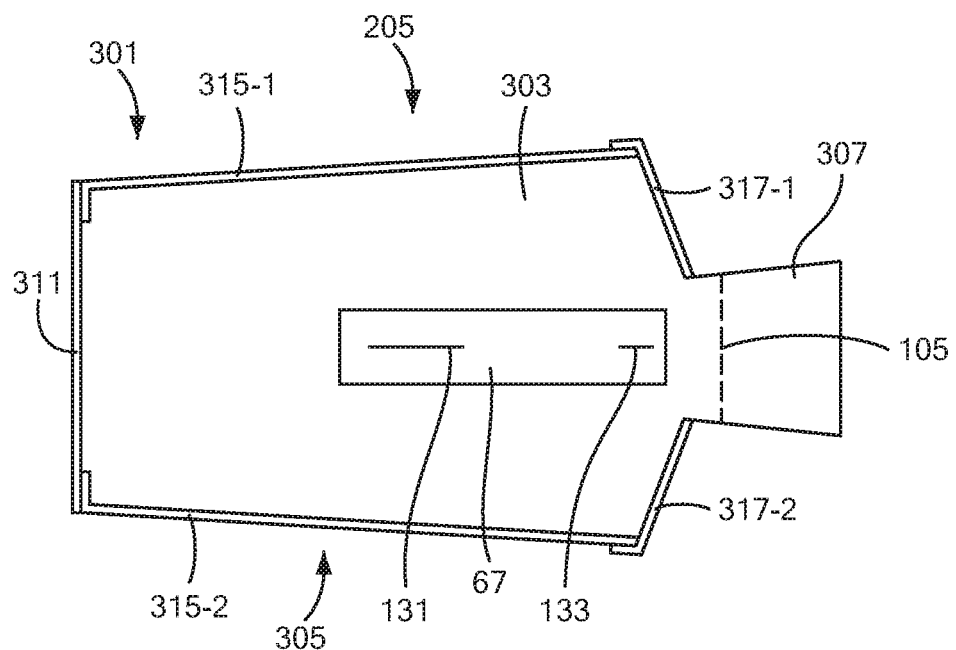
FIGS. 12(a) and 12(b) are top and side views, respectively, of the second drape shown in FIG. 9.
Figure 12B:
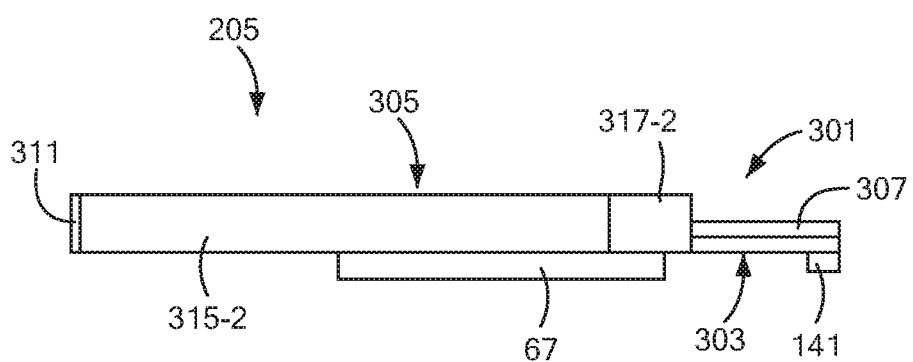

Second drape 205, which is also shown in FIGS. 12(a) and 12(b), may be similar in many respects to second drape 15. (For clarity, certain details of second drape 205 that are discussed elsewhere in this application or that are not critical to an understanding of the invention may not be shown in all of FIGS. 12(a) and 12(b) or may be shown therein in a simplified manner.) One difference between drape 205 and drape 15 may be that drape 205 may comprise a first part 301, instead of first part 65. First part 301 may be configured to comprise a mat portion 303, which may be a generally planar yet flexible structure, and a skirt portion 305, which may extend upwardly from mat portion 303 around at least a portion of the periphery of mat portion 303. Mat portion 303 may be configured similarly to first part 65 of drape 15. Skirt portion 305, which may surround all but a distal portion 307 of mat portion 303, may be useful in keeping fluids from running over the sides and proximal end of mat portion 303, particularly where the flow rate of a fluid across mat portion 303 exceeds the absorbency rate of the fluid by mat portion 303. In the present embodiment, skirt portion 305 may have a height of approximately 1.0 inch and may comprise a distal end portion 311, a pair of side portions 315-1 and 315-2, and a pair of proximal end portions 317-1 and 317-2. Side portion 315-1 may be adhered or otherwise secured at one end to a first end of distal end portion 311 and may be adhered or otherwise secured at another end to an end of proximal end portion 317-1. Side portion 315-2 may be adhered or otherwise secured at one end to a second end of distal end portion 311 and may be adhered or otherwise secured at another end to an end of proximal end portion 317-2.

First member 301 may be a laminated structure comprising two layers similar to layers 111 and 113 of first part 65 and may be constructed from a single sheet of material in a manner analogous to that described above for making first member 211 of first drape 203 using sheet 231. Alternatively, first member 301 need not be a unitary structure, and mat portion 303 and skirt portion 305 may be constructed from two or more separate pieces.

Third drape 207 may be identical to third drape 17.

Draping system 201 may be installed on a medical apparatus in a similar fashion to that described above for draping system 11.

As can readily be appreciated, other embodiments of the present invention may comprise combinations or variations of draping systems 11 and 201. For example, in an alternative embodiment (not shown), the draping system may comprise drape 203 and drape 15 or may comprise drape 13 and drape 205.

The embodiments of the present invention described above are intended to be merely exemplary and those skilled in the art shall be able to make numerous variations and modifications to it without departing from the spirit of the present invention. All such variations and modifications are intended to be within the scope of the present invention.

What is claimed is:

1. A draping system suitable for use with a prone biopsy system, the prone biopsy system comprising a paddle mount, the draping system comprising a first drape, the first drape comprising a first mat and a protuberance, the protuberance extending upwardly from the first mat and having a completely enclosed distal end spaced apart from the first mat such that the protuberance is configured to be inserted over the paddle mount, wherein the first mat and the protuberance comprise different materials.

2. The draping system as claimed in claim 1 wherein the protuberance is optically transparent or translucent.

3. The draping system as claimed in claim 2 wherein the protuberance is made of a clear polymer film.

4. The draping system as claimed in claim 1 wherein the first mat comprises a length, wherein the protuberance comprises a length, a width and a perimeter, wherein the length of the protuberance is perpendicular to the length of the first mat, wherein the protuberance is positioned off-center relative to the length of the first mat so as to be disposed closer to a first end of the first mat than to a second end of the first mat, wherein the width of the protuberance is substantially less than the length of the first mat, and wherein the perimeter of the protuberance is completely surrounded by and sealed to the first mat.

5. The draping system as claimed in claim 1 wherein the first mat comprises an absorbent material.

6. The draping system as claimed in claim 1 wherein the first drape further comprises a first skirt, the first skirt extending upwardly from the first mat around at least a portion of a periphery of the first mat.

7. The draping system as claimed in claim 1 wherein the first mat is configured to form at least one fold when the paddle mount is moved to a breast compressing position.

8. The draping system as claimed in claim 1 wherein the first drape further comprises a strip of absorbent material, the strip of absorbent material being secured to the first mat, the strip of absorbent material comprising a higher absorbing material than material of the first mat.

9. The draping system as claimed in claim 8 wherein the strip of absorbent material is disposed along a length of the protuberance and is positioned at a location intermediate the protuberance and an end of the first mat so as to be positioned below a breast when the paddle mount is moved to a breast compressing position.

10. A draping system suitable for use with a prone biopsy system, the prone biopsy system comprising a paddle mount and a compression paddle, the compression paddle being mountable on the paddle mount, the draping system comprising:
   a first drape, the first drape comprising a first mat and a protuberance, the protuberance extending upwardly from the first mat and being configured to be inserted over the paddle mount, wherein the first mat and the protuberance comprise different materials; and
   a second drape, the second drape comprising a second mat, the second mat comprising a distal end configured to be fixedly mounted on the compression paddle when the compression paddle is mounted on the paddle mount.

11. The draping system as claimed in claim 10 wherein the prone biopsy system further comprises a stage arm assembly and wherein the second mat is configured to cover at least a portion of the stage arm assembly, the second mat being provided with one or more perforations for use in separating the second mat into a plurality of pieces.

12. The draping system as claimed in claim 10 wherein the second drape further comprises a second skirt, the second skirt extending upwardly from the second mat around at least a portion of a periphery of the second mat.

13. The draping system as claimed in claim 1 wherein the first mat comprises a laminate of an absorbent nonwoven fabric and a first liquid-impervious material and wherein the protuberance comprises a second liquid-impervious material, the first and second liquid-impervious materials being heat-sealable to one another.

14. A draping system suitable for use with a prone biopsy system, the prone biopsy system comprising a paddle mount, the draping system comprising a first drape, the first drape comprising a first member and a second member, the first member comprising a first mat having a first transverse opening, the second member comprising a protuberance and a flange, wherein the protuberance extends substantially perpendicularly relative to the flange and includes a completely enclosed distal end spaced apart from the flange, the first member coupled to the second member such that the protuberance extends through the first transverse opening of the first mat and being configured to receive the paddle mount, the flange being used to couple the protuberance to the first mat.

15. The draping system as claimed in claim 14 wherein the flange and the first mat form a liquid-tight seal around an entirety of the protuberance.

16. The draping system as claimed in claim 14 wherein the first member further comprises a first skirt, the first skirt extending upwardly from the first mat around at least a portion of a periphery of the first mat.

17. The draping system as claimed in claim 14 wherein the first member comprises a laminate of an absorbent nonwoven fabric and a first liquid-impervious material and wherein the second member comprises a second liquid-impervious material, the first and second liquid-impervious materials being heat-sealable to one another.

18. The draping system as claimed in claim 17 wherein the second member comprises a clear, flexible polymer film, whereby mounting of a compression paddle to the paddle mount after the paddle mount has been covered by the protuberance is not impeded and whereby operation of a Hall-effect sensing mechanism disposed within the paddle mount for detecting the compression paddle is not impeded.

19. The draping system as claimed in claim 14 wherein the prone breast biopsy system further comprises a breast support platform behind which an image receptor is positioned and wherein the first drape further comprises a strip of adhesive tape for securing a first end of the first mat to the breast support platform just below the image receptor, wherein the first mat is dimensioned so as to form at least one fold below a compressed breast when the paddle mount is moved to a breast compressing position, and wherein the first drape further comprises a strip of absorbent material secured to the first mat, the strip of absorbent material being disposed on the first mat so as to be positioned below the compressed breast.

20. The draping system as claimed in claim 14 wherein the prone biopsy system further comprises a compression paddle and a stage arm assembly, the compression paddle being mountable on the paddle mount, the draping system further comprising a second drape, the second drape comprising a second mat, the second mat being configured to cover at least a portion of the stage arm assembly, the second mat comprising a distal end, the distal end being configured to be fixedly mounted on the compression paddle when the compression paddle is mounted on the paddle mount, the second mat further comprising one or more perforations for use in separating the second mat into a plurality of pieces, the second drape further comprising a second skirt, the second skirt extending upwardly from the second mat around at least a portion of an periphery of the second mat.

* * * * *